United States Patent
Dawley et al.

(10) Patent No.: US 6,473,169 B1
(45) Date of Patent: Oct. 29, 2002

(54) INTEGRATED LEAK AND VISION INSPECTION SYSTEM

(75) Inventors: James M. Dawley, Dousman; Andrew T. Jakubowski, Milwaukee; Michael F. Meckl, Kewaskum, all of WI (US)

(73) Assignee: Air Logic Power Systems, Inc., Milwaukee, WI (US)

( * ) Notice: Subject to any disclaimer, the term of this patent is extended or adjusted under 35 U.S.C. 154(b) by 0 days.

(21) Appl. No.: 09/563,960

(22) Filed: May 3, 2000

(51) Int. Cl.$^7$ ............................ G01N 21/00; G01N 9/04
(52) U.S. Cl. ................. 356/239.4; 250/223 B
(58) Field of Search .......................... 356/239.4–240.1; 250/223 B, 223 R, 556, 227.2

(56) References Cited

U.S. PATENT DOCUMENTS

| | | |
|---|---|---|
| 3,957,154 A | 5/1976 | Shiba |
| 4,146,134 A | 3/1979 | Keen et al. |
| 4,158,625 A | 6/1979 | Takahashi et al. |
| 4,221,961 A | 9/1980 | Peyton |
| 4,241,256 A | 12/1980 | Tagaya et al. |
| 4,378,495 A | 3/1983 | Miller |
| 4,399,357 A | 8/1983 | Dorf et al. |
| 4,584,469 A | 4/1986 | Lovalenti |
| 4,610,542 A | 9/1986 | Ringlien |
| 4,620,090 A * | 10/1986 | Ducloux ................. 250/223 B |
| 4,636,635 A | 1/1987 | Krönseder |
| 4,736,861 A | 4/1988 | Basili |
| 4,831,250 A | 5/1989 | Fukuchi et al. |
| 4,847,940 A | 7/1989 | Bradbury |
| 4,852,415 A | 8/1989 | Bogatzki et al. |
| 4,866,263 A | 9/1989 | Fukuchi |
| 4,882,498 A | 11/1989 | Cochran et al. |
| 4,912,318 A | 3/1990 | Kajiura et al. |
| 4,924,083 A | 5/1990 | Ishikawa et al. |
| 4,948,956 A | 8/1990 | Fukuchi |
| 4,959,537 A | 9/1990 | Kimoto et al. |
| 4,975,568 A | 12/1990 | Taniguchi et al. |
| 5,045,688 A | 9/1991 | Domenico et al. |
| 5,072,107 A | 12/1991 | Apter |
| 5,073,708 A | 12/1991 | Matsumoto et al. |
| 5,095,204 A | 3/1992 | Novini |
| 5,126,556 A | 6/1992 | Domenico et al. |
| 5,136,157 A | 8/1992 | Apter et al. |
| 5,200,801 A | 4/1993 | Juvinall et al. |
| 5,349,435 A | 9/1994 | Hall et al. |
| 5,436,722 A | 7/1995 | Baldwin |
| 5,440,385 A | 8/1995 | Fein et al. |
| 5,442,446 A * | 8/1995 | Gerber et al. ................ 356/428 |
| 5,466,927 A | 11/1995 | Kohler et al. |

(List continued on next page.)

Primary Examiner—Michael P. Stafira
(74) Attorney, Agent, or Firm—William K. Baxter; Godfrey & Kahn, S.C.

(57) ABSTRACT

An integrated leak and vision inspection system is provided that accurately and efficiently inspects a bottle or other container for manufacturing defects. The system provides a series of visual inspection stations with cameras and lighting that are integrated onto a rotary inspection system for on-line inspection of containers. A microprocessor in data communication with each of the inspection stations receives and analyzes image data of the particular area or parameter of the container being inspected or tested, and generates data relating to the container based upon predetermined criteria. The stations are arranged to provide an integrated and fully automated and efficient inspection system. In the preferred embodiment, the system is structured with a first station integrated with an entry starwheel to inspect the top seal surface of the container. As the container moves out of the starwheel, a probe from a leak test assembly seals the container opening and the container is tested for leaks as it moves on a main turntable into and through a second station to visually inspect the neck finish. The container is then transported on the turntable to a third station integrated with an exit starwheel to visually inspect the base of the container. The exit starwheel shifts the container onto the line conveyor to a reject station, which removes any containers that are below the set standards.

27 Claims, 18 Drawing Sheets

U.S. PATENT DOCUMENTS

| | | |
|---|---|---|
| 5,591,462 A | 1/1997 | Darling et al. |
| 5,591,899 A | 1/1997 | Griesbeck |
| 5,610,391 A | 3/1997 | Ringlien |
| 5,637,864 A | 6/1997 | Nicks et al. |
| 5,719,679 A | 2/1998 | Shimizu et al. |
| 5,898,169 A * | 4/1999 | Nordbryhn ............... 250/223 B |
| 6,239,870 B1 * | 5/2001 | Heuft ...................... 356/239.5 |
| 6,256,095 B1 * | 7/2001 | Ringlien ................. 356/239.4 |

* cited by examiner

INTEGRATED LEAK AND VISION INSPECTION SYSTEM

FIELD OF THE INVENTION

This application relates to a system used for inspecting and testing containers for defects. More particularly, the invention relates to an integrated automated inspection system having multiple test systems for testing and visually inspecting plastic containers.

BACKGROUND OF THE INVENTION

Machine vision inspections provide inspection of containers for defects that may arise from the manufacturing processes. Some inspections are specific to PET container processes, such as soda and other beverage bottles. Most are also applicable to other container materials such as HDPE, LDPE, and PVC.

Most PET containers are produced from an injection-molded preform, which are converted by a molding machine into a final container shape. Some molding machines combine preform injection with blowing the preform into a final container shape in a single machine. The large majority of PET containers are blow molded in a completely separate operation in which the preform is re-heated, then mechanically stretched and blown into a final container shape. Other plastic materials are typically extruded into a parison or tube of hot plastic, which, while still hot and pliable, is clamped by a mold and blown into a final shape. This final shape often includes excess plastic at the top and bottom of the container that must be trimmed off.

Machine vision inspections that are commonly done on different types of plastic containers include inspection of the top seal surface, dimensions of the finish area, neck folds, sidewall contamination, and the base area. The top seal surface (TSS) is inspected on PET containers for mechanical damage and "short shots," which is a sink in the TSS due to injecting insufficient plastic into the preform mold. Inspection of the TSS reveals ovality defects, the extent to which the TSS deviates from a circular shape, which may result from process problems. Dimensional inspection of the finish area involves measuring thread diameters and nearby features. The shoulder area below the neck ring of PET containers can be inspected for neck folds. Bottle sidewalls can be inspected for foreign object contamination. The base area of the bottle is commonly inspected only on PET beverage containers.

Machine vision inspection requires consistent positioning of the container, mounting for cameras and lighting, and means of ejecting containers that fail inspection. Providing a separate piece of equipment to meet these requirements takes up plant floor space which, for most container manufacturers, is perennially in short supply. In addition, each separate piece of machinery that must "handle" the container requires tooling, set-up time, and maintenance.

Therefore, an object of the invention is to provide an integrated leak and vision inspection system that overcomes the disadvantages of known inspection systems.

SUMMARY OF THE INVENTION

These and other objects are achieved by the present invention, which provides an integrated leak and vision inspection system, and methods of using the system to inspect containers for defects.

The system provides multiple operator stations and camera/lighting enclosures that are integrated onto a rotary inspection system for on-line inspection of containers to efficiently and accurately test and inspect each container. The containers are continuously fed from a conveyor belt onto a turntable via a timing screw and an infeed starwheel. The containers then pass through a series of vision inspection stations that can include inspection of the top seal surface, the base, finish dimensions, sidewalls, and neck folds. In a preferred embodiment, the system integrates the vision inspection systems with a leak testing assembly. An exit starwheel feeds the containers back onto the conveyor where defective containers are automatically ejected.

Each vision inspection assembly includes an electronic camera and lighting that are positioned as required according to the particular inspection being performed. The system further includes image acquisition/processing hardware and software.

The present vision inspection system provides an economical, fully integrated piece of equipment for on-line vision inspection of containers. The system provides consistent container positioning and testing. The integration of test and inspection assemblies significantly reduces space requirements for the system layout, as well as assembly time and maintenance. The fully-automated inspection system invention provides an efficient, compact system for inspecting and testing containers.

BRIEF DESCRIPTION OF THE DRAWINGS

Throughout the following views, reference numerals will be used on the drawings, and the same reference numerals will be used throughout the several views and in the description to indicate same or like parts of the invention.

DETAILED DESCRIPTION OF THE INVENTION

Figure 1:
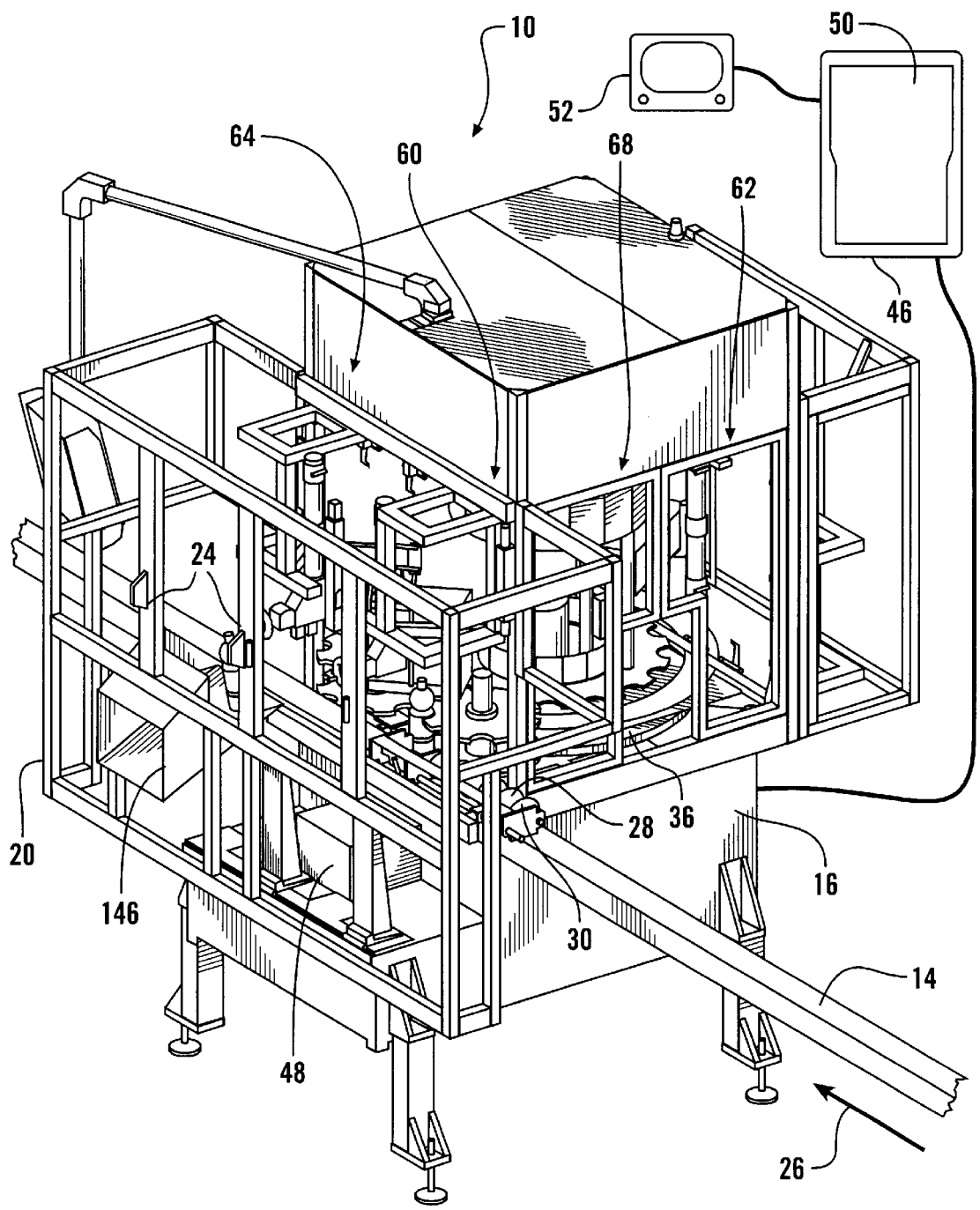
FIG. 1 is a perspective view of an embodiment of the integrated leak and vision inspection system of the invention, with the doors and front and rear guards in place.
Figure 2:
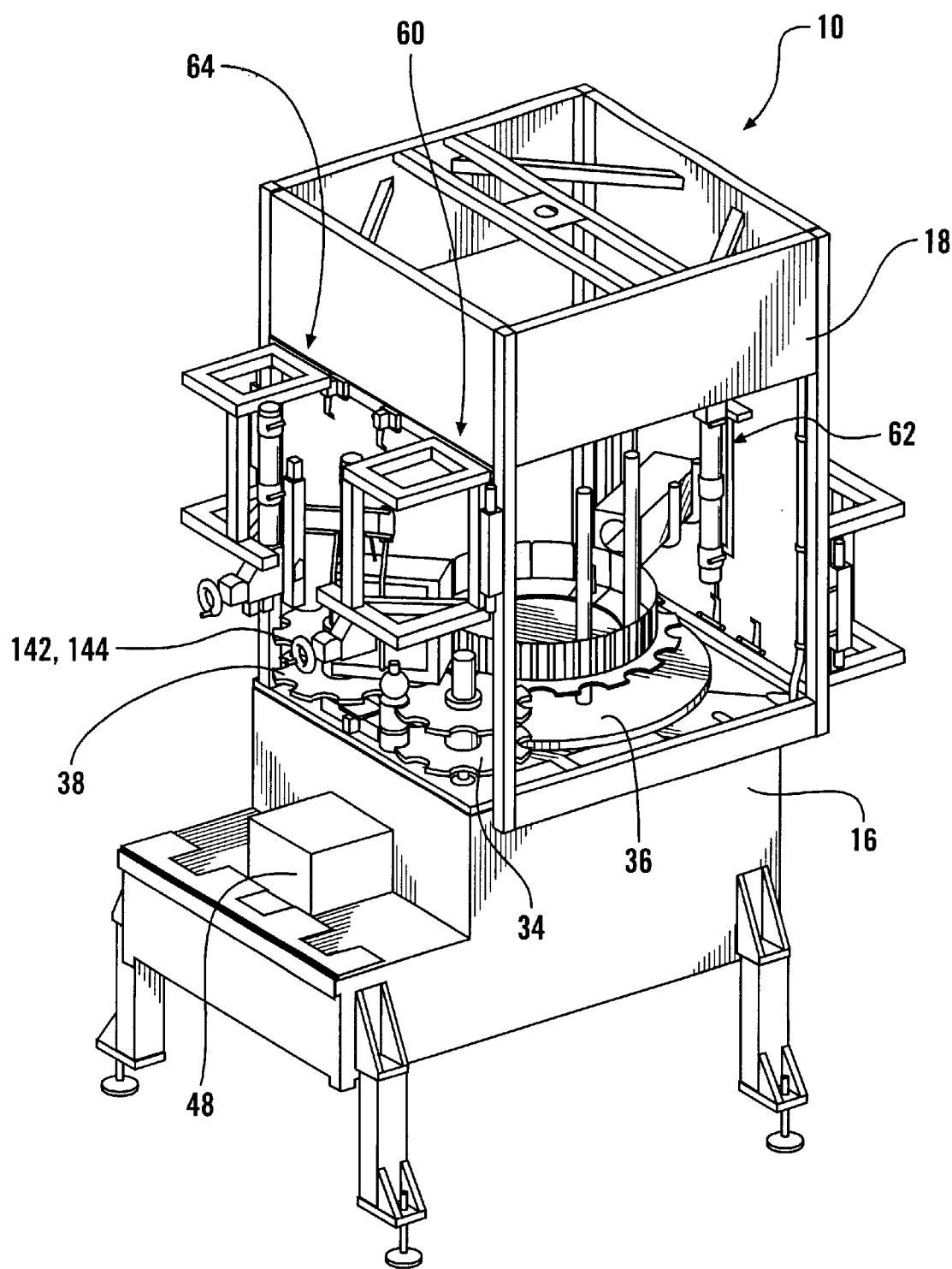
FIG. 2 is a perspective view of the system shown in FIG. 1, with the guards and doors removed.
Figure 3:
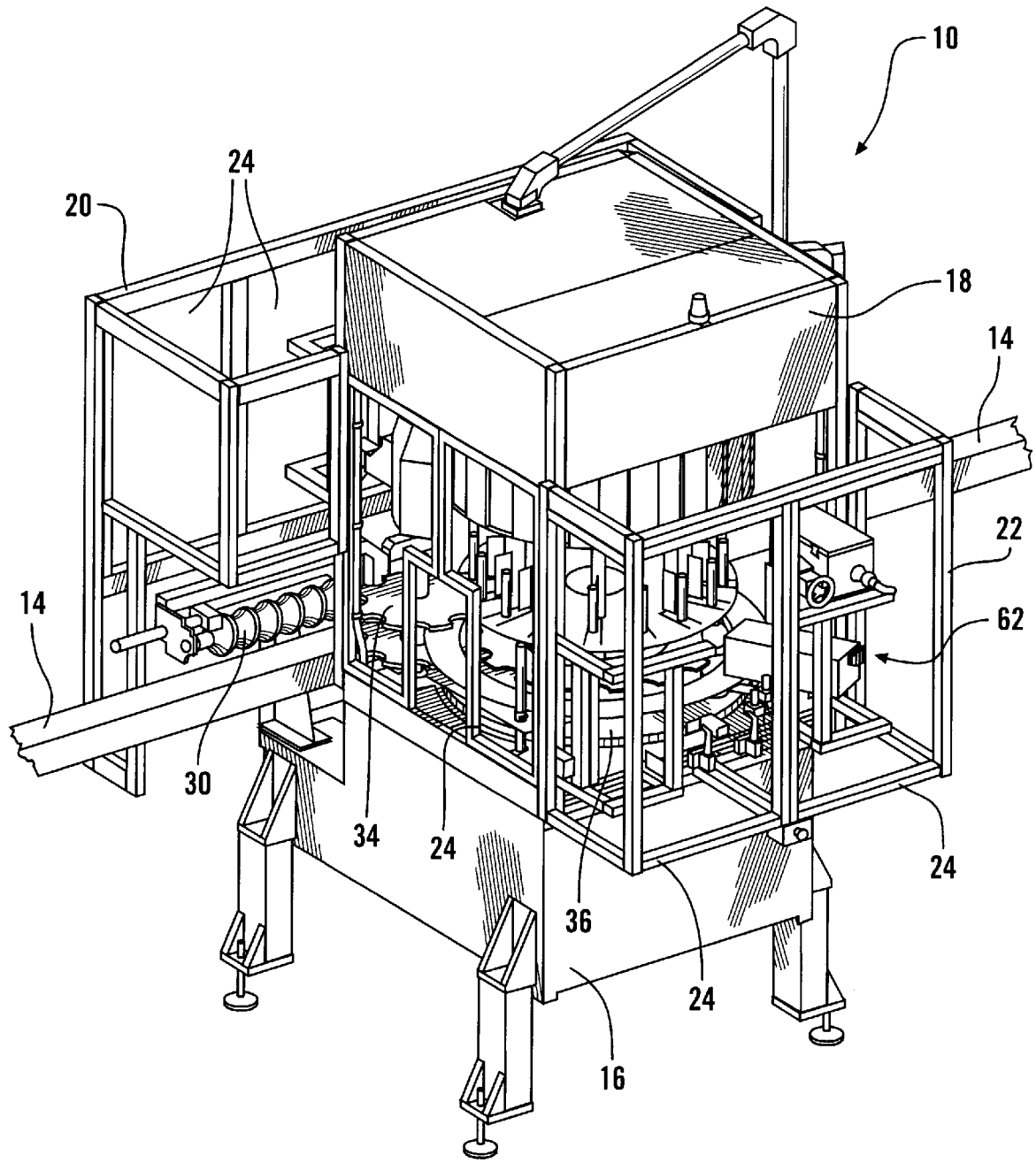
FIG. 3 is a perspective rearward view of the system shown in FIG. 1.
Figure 4:
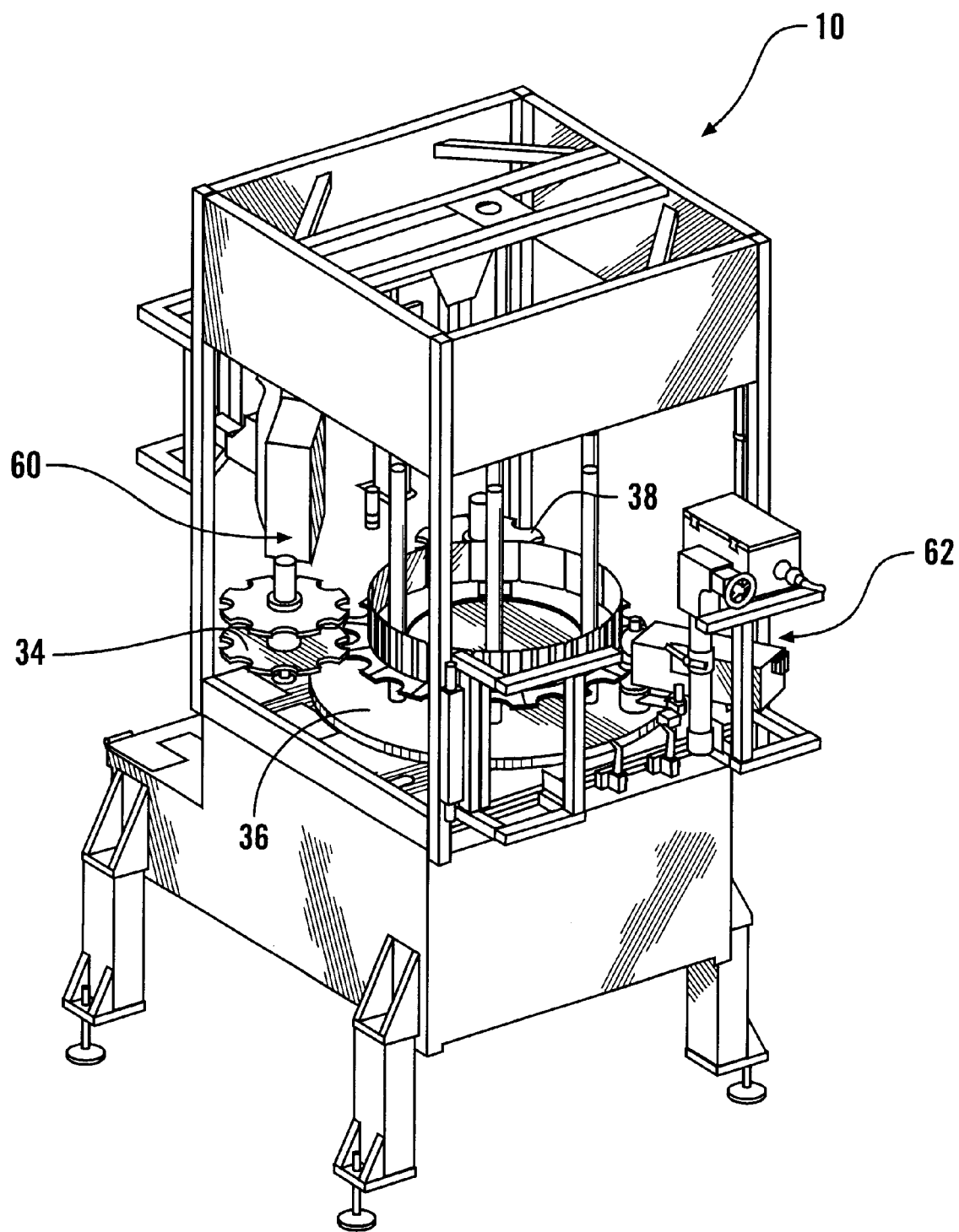
FIG. 4 is a perspective view of the system shown in FIG. 3, with the guards and doors removed.
Figure 5:
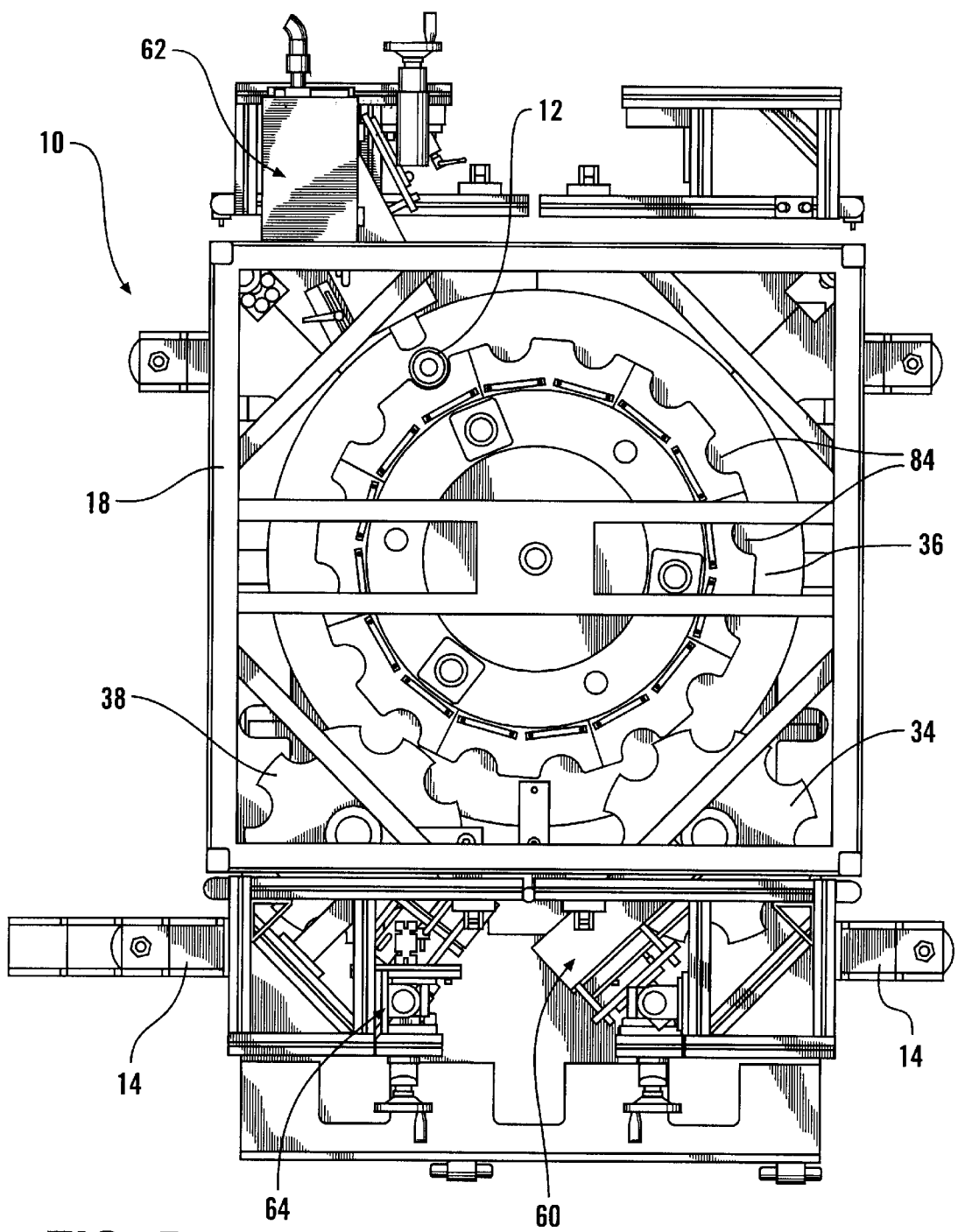
FIG. 5 is a top plan view of the system shown in FIGS. 2 and 4, with the guards and doors removed.
Figure 6:
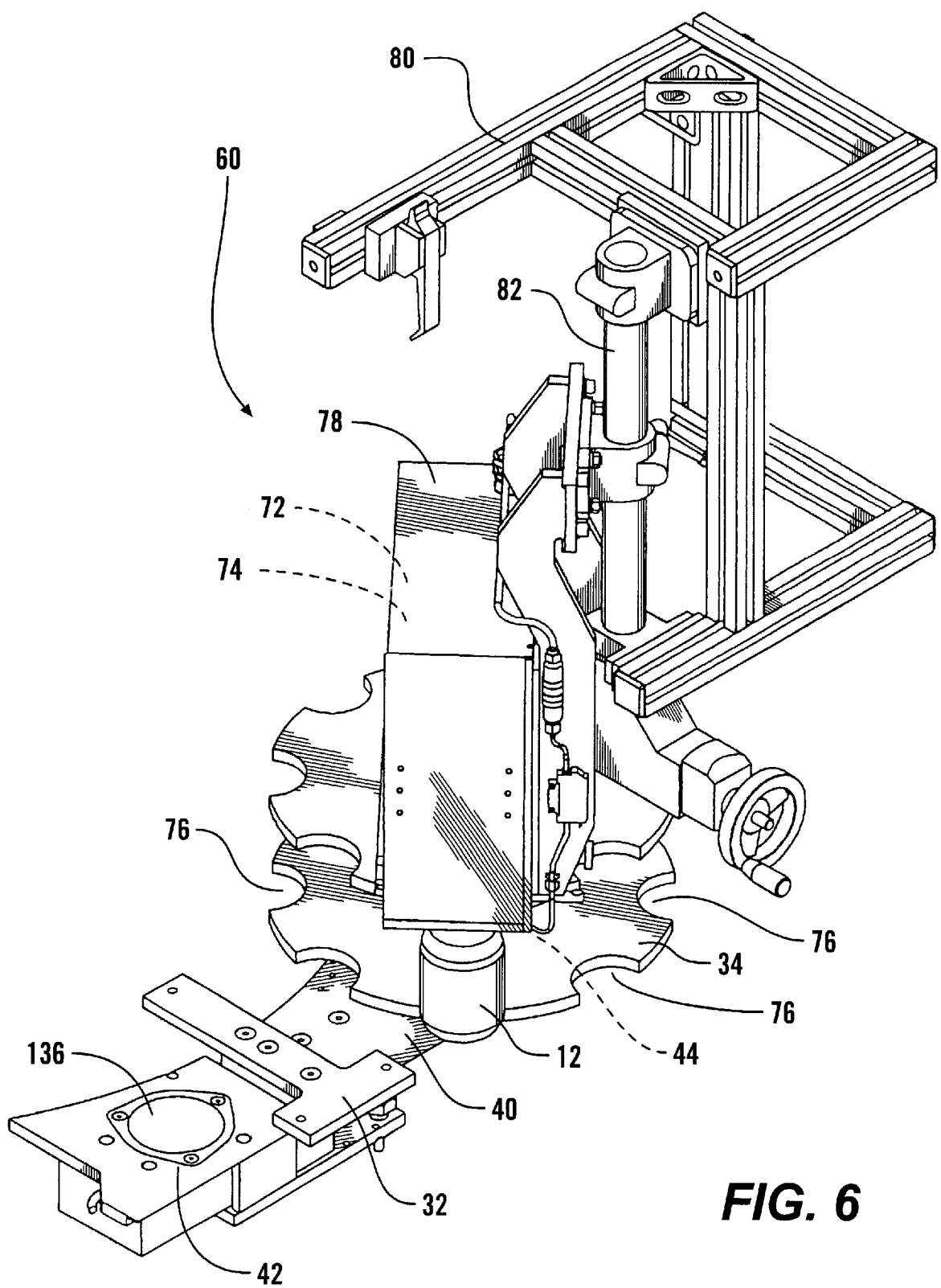
FIG. 6 is a perspective view of the top seal surface vision inspection assembly of the system shown in FIG. 1.

The invention provides an integrated rotary control leak and vision inspection system for transparent and translucent plastic bottles or containers, including PET stretch-molded containers and HDPE containers. An embodiment of the system, designated generally as 10, is depicted in FIGS. 1–16. The system 10 includes three main components: a vision inspection control unit 46; a leak test control unit 66; and a programmable logic controller (PLC) 48. Each of these units are connected together and communicate with each other over a data bus. The vision inspection control unit 46 accepts or rejects containers and communicates that information to the PLC 48. The leak test control unit 66 tests for leaks in a container and sends that information to the PLC 48. The PLC 48 determines whether to accept or reject a container.

The system 10 combines assemblies to inspect the base, top seal surface (TSS), and neck finish of a vertically standing container 12, with a pressure or leak test system. Containers 12 are transported off of a conveyor line 14 and into the system where the desired inspections and tests of the container take place. The rotary control system 10 tracks containers as they move through the various inspection stations. Data about number and type of all vision inspection rejections is provided to operators at a single display station 52. Defective containers are automatically rejected from the conveyor line 14 upon their exit from the inspection system. The maximum speed range of the system 10 depends on the container size, required handling, configuration, conveyor speed range, and desired leak test sensitivity, generally between 10–30 bottles per minute (BPM) per test station for 2-gallon to 2-ounce container sizes.

The framing structure of the system 10 includes a base unit 16, an enclosed frame upper unit 18, a line conveyor 14, and front and rear guard units 20,22 that are mounted to the upper unit 18. The guard units are enclosed frames with hinged doors or windows 24, preferably with built-in safety switches, which enclose but allow access to the system mechanisms and inspection assemblies housed inside. The front guard unit 20 also encloses the line conveyor 14 where the containers 12 move into and out of the inspection system 10.

In general, the containers 12 move along the line conveyer 14 in the direction of arrow 26, and are closely spaced as they arrive at a separator timing screw 30 which handles and separates the containers 12 by a short distance on the infeed 28 of the system 10. The containers sequentially move into an infeed starwheel 34 or other like infeed mechanism that transports the containers off of the production line conveyor 14 and onto a continuously moving rotary platform 36 or turntable that carries the containers through the system 10. An exit starwheel 38 or other like exit mechanism transports containers off of the inspection turntable 36 and back on to the production line conveyor 14. A center guide 32 provides a contact surface to maintain bottle position within the starwheels 34, 38. A deadplate 40, 42 at the infeed and the exit starwheels 34, 38 supports the container during the transition between the line conveyor 14 and the turntable 36.

Fiber-optic, trigger photoeyes (photocell) 44 are used at the gate mechanism 28, the individual vision inspection stations, and the reject station. The photoeyes 44 are adjusted as a unit for height and in-out adjustments, and for spacing adjustments. As the container approaches the gate 28 or station, it breaks a beam from the photoeye 44, which initiates the particular operation.

The system 10 is electronically linked to a control unit 46 that includes a data processor 50 such as a microprocessor or personal computer for storing and analyzing data received from the vision inspection assemblies. Breaking the beam of the photoeye 44 sends a signal to the PLC 48 and the data processor 50 to signal the presence of a container to be tested. This puts a "1" in a shift register in the PLC to track the position of a particular container as it moves through the system 10 and to the rejection point 142.

The PLC 48 and frequency drive control the speed and motion of the conveyor 14 and turntable 36, a mode selection switch, a gate timing switch, the two starwheels 34, 38, and the timing screw 30. The starwheels and timing screw include adjustable clutches that work in conjunction with the PLC 48 to control machine motion and an integrated safety brake system. The software used in the PLC controls the frequency drive by turning on either an "increase" or "decrease" signal and monitoring a speed feedback signal from a rotary encoder attached to one of the starwheel drive shafts.

The microprocessor 50 is adapted to acquire and store pixel data, and develop a histogram based on the pixels for each inspection. The microprocessor 50 is programmed to initiate an inspection operation when a signal is received from the photoeye 44 that a container is in the station. At each vision inspection station, the passage of the container 12 in front of the photoeye 44 triggers the light source and camera. The light is synchronized with a field sync signal from the camera. The camera, which is preferably a video camera, takes an image(s) of the portion of the container being inspected, and a data processor converts the image(s) to numeric digital images. The microprocessor receives the data signals from a data signaling device connected to the camera, which are representative of the camera image of the container. The microprocessor is set with acceptable parameters for a particular inspection test, and compares that value to a desired, preprogrammed value in its memory.

The microprocessor 50 is connected through a communications link to a data display unit 52 such as a printer and/or a terminal display such as a liquid crystal display, an electronic digital display, or other visual indicator for displaying and/or printing out the data from a particular test or inspection. If the value is outside of a set parameter for that feature of the container, the microprocessor 50 will record the value for the tracked container. The microprocessor 50 will also send a signal to the PLC indicating that the container should be ejected from the conveyor 14 at location 142.

The machine vision (MV) inspection software is composed of a number of algorithms that analyze the image array data as required by the individual inspections. Generally, the software converts image data to engineering units and allows setting appropriate rejection values.

Mechanical and optical requirements of the different types of vision inspections influence the location of a particular inspection assembly in the system 10. The vision inspection assemblies can be located at the infeed timing screw 30 (although this location is not as desirable because bottle positioning is least consistent there, especially at higher speeds), at both the infeed and exit starwheels 34, 38 with container position being controlled by the starwheel and centerguide 32, and at multiple locations on the main turntable 36.

For a particular vision inspection, the optimal relative positions of the camera, lighting and container are determined in order to provide proper illumination of the container and acquire a good inspection image. The arrangement of the camera and lighting is located relative to the path of the moving containers in such a way that the containers will be presented in a consistent relationship to the camera/lighting assembly at the moment that the inspection image is taken. The dimensional measurements of the image are recorded as pixels and, if appropriate, converted to dimensional units (inches or millimeters).

Depicted in the figures is an inspection system 10 that is fully automated for on-line container inspection. As shown, the system 10 includes vision inspection assemblies for top seal surface inspection 60, neck finish inspection 62, and base inspection 64, and an assembly for leak testing 66. Additional assemblies for sidewall and neck fold inspections can be integrated into the system, as discussed below.

Top Seal Surface (TSS) Inspection

A top seal surface (TSS) inspection assembly 60 is depicted in FIGS. 6–10. Inspection of the top seal 70 of a container 12 requires both the camera 72 and the light source 74 to be located above the container. The optimal position for this inspection is at the entry or infeed starwheel 34 as shown, where the bottle is controlled in the infeed starwheel. The shape of the pocket 76 and size of the infeed starwheel 34 are adapted to optimize bottle position for the vision inspection.

The TSS inspection system 60 views the container 12 to accurately gauge the seal surface 70, and detect seal surface gaps, short-shot moldings, seal surface narrowing, overall width of seal surface, average seal surface width, and ovality faults. The TSS inspection can employ a co-axially arranged lighting and imaging set-up for which the camera 72 and the light source 74 are located directly above the container 12 (FIG. 8), or a glancing illumination set-up for which the camera 72 and the light source 74 are mounted at equal angles from the vertical axis of the container (FIG. 9). The glancing illumination technique offers advantages by causing some types of TSS defects such as narrowing of the seal surface, to be more evident in the camera image.

Figure 7:
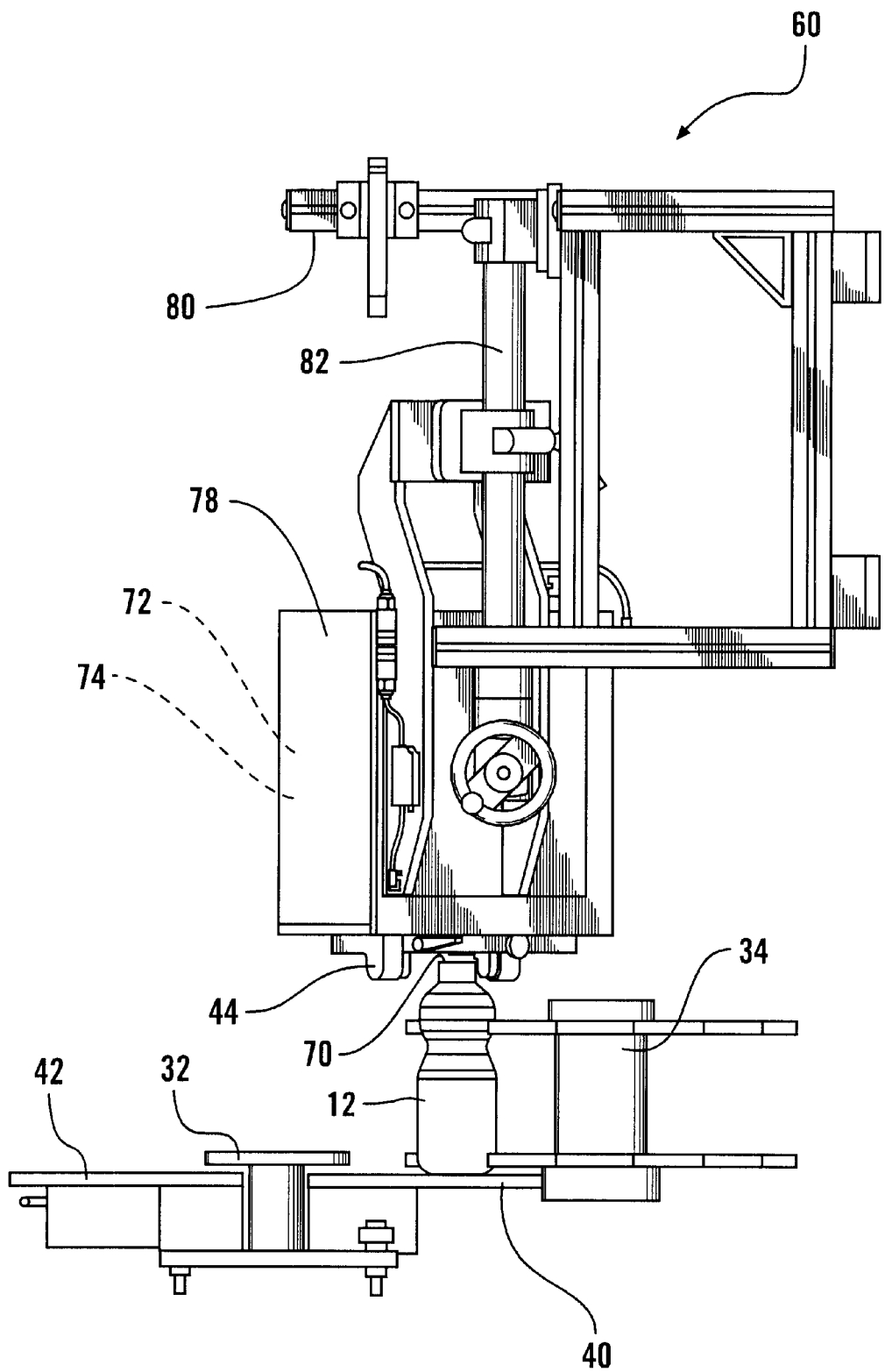
FIG. 7 is a side elevational view of the assembly shown in FIG. 6.
Figure 8:
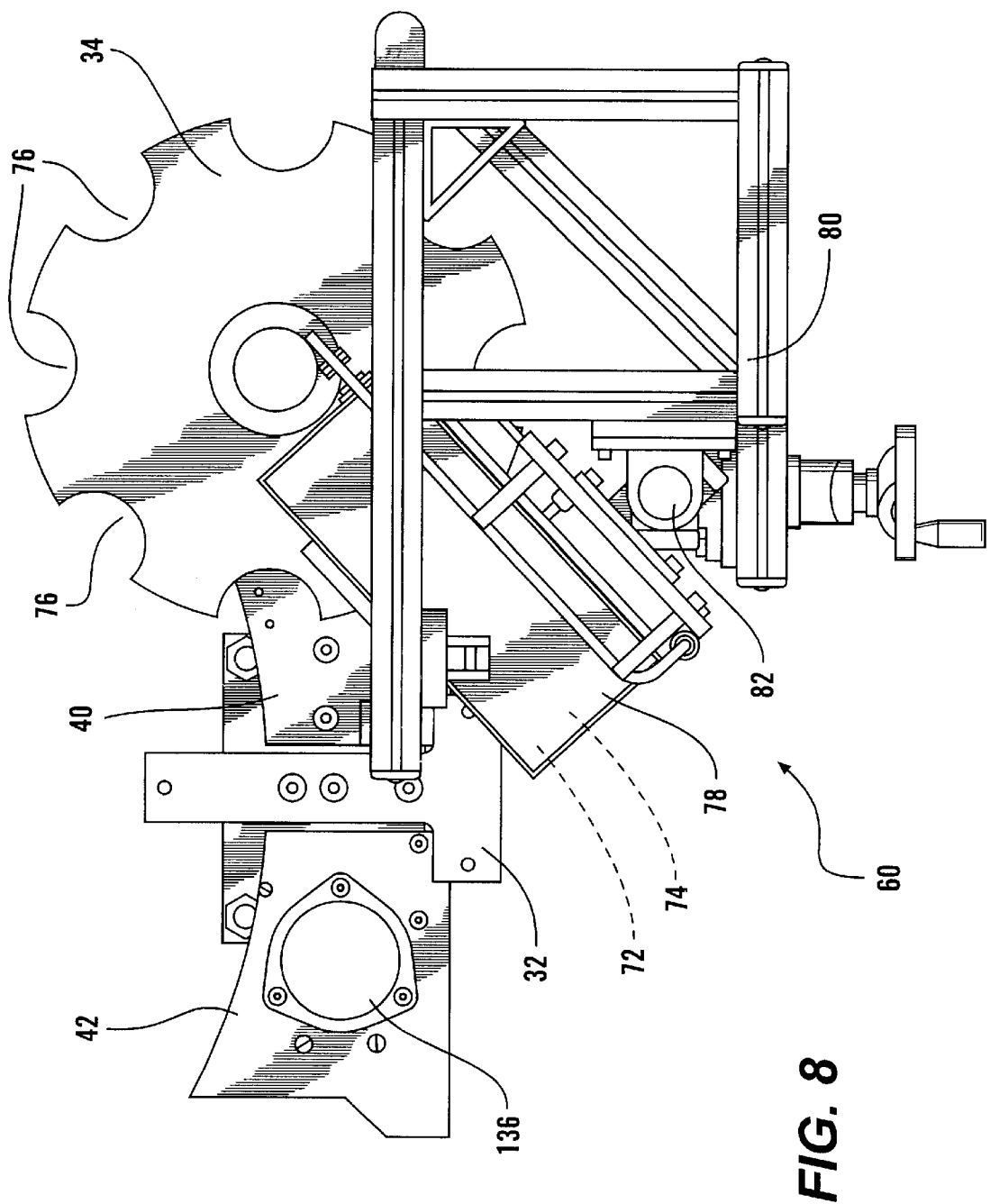
FIG. 8 is a top plan view of the assembly shown in FIG. 6.
Figure 9:
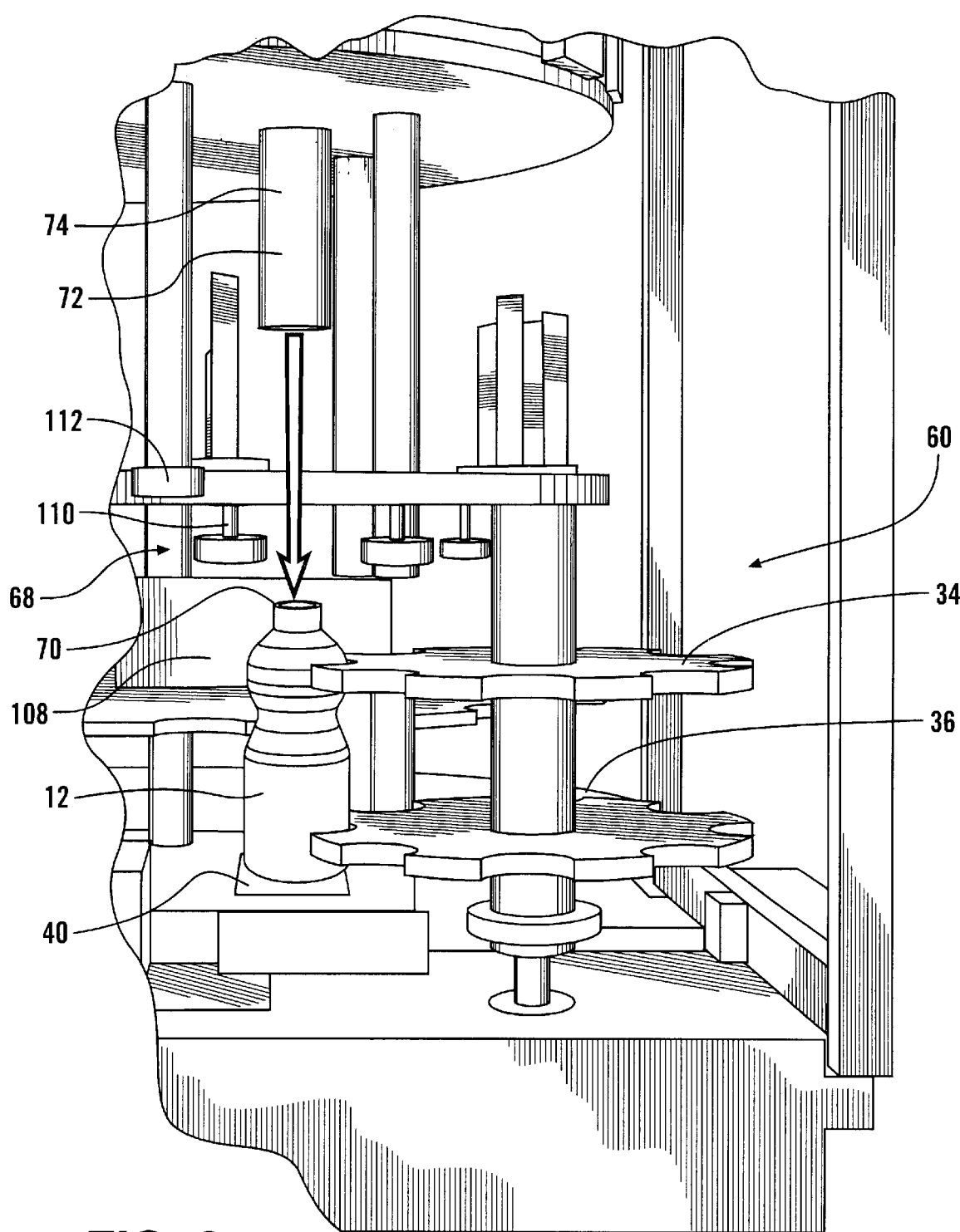
FIG. 9 is a side elevational view of the assembly shown in FIG. 6, showing co-axially arranged light source and camera.
Figure 10:
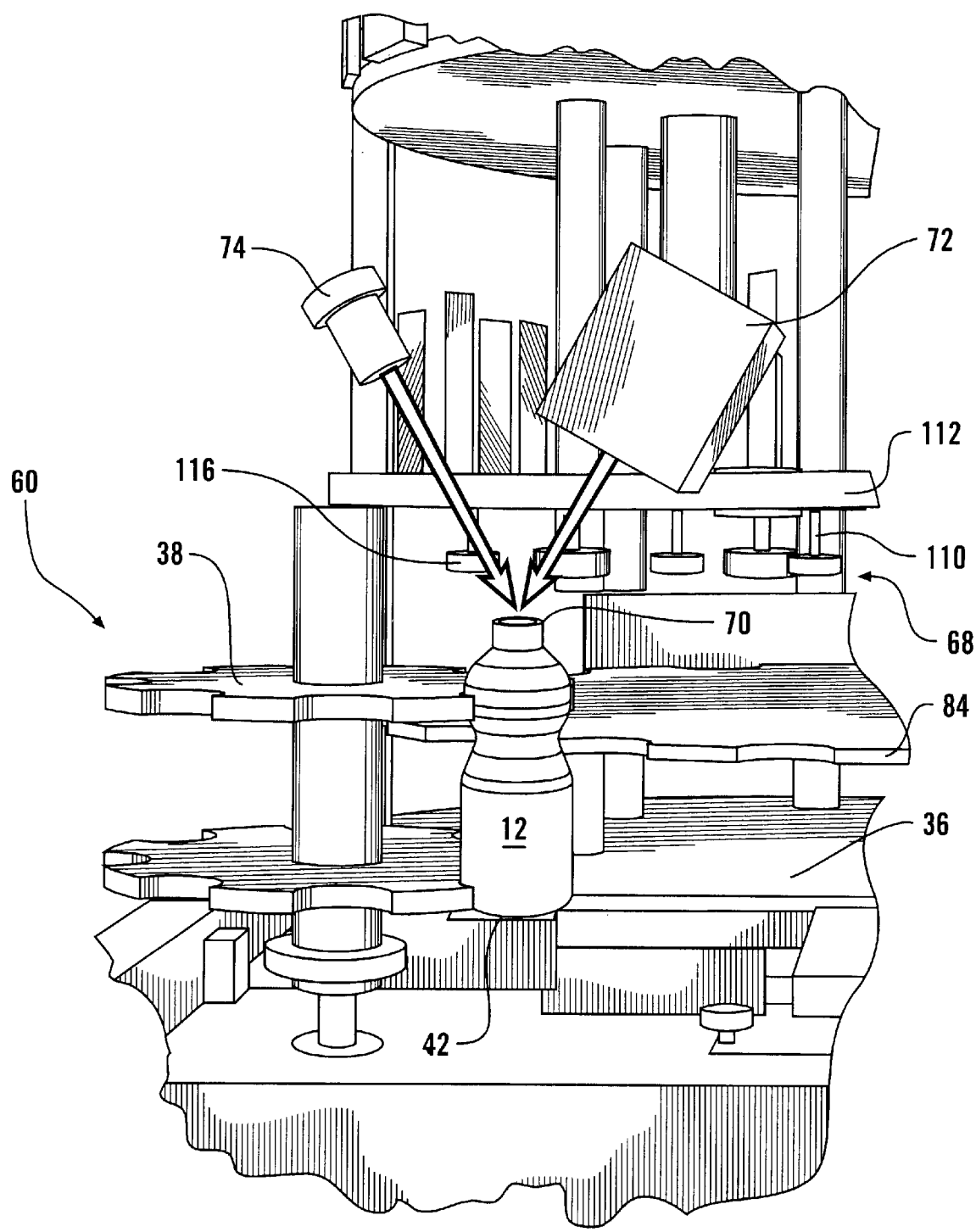
FIG. 10 is a side elevational view of the top seal surface vision set-up at the exit starwheel, and showing a glancing illumination/camera set-up.
Figure 11:
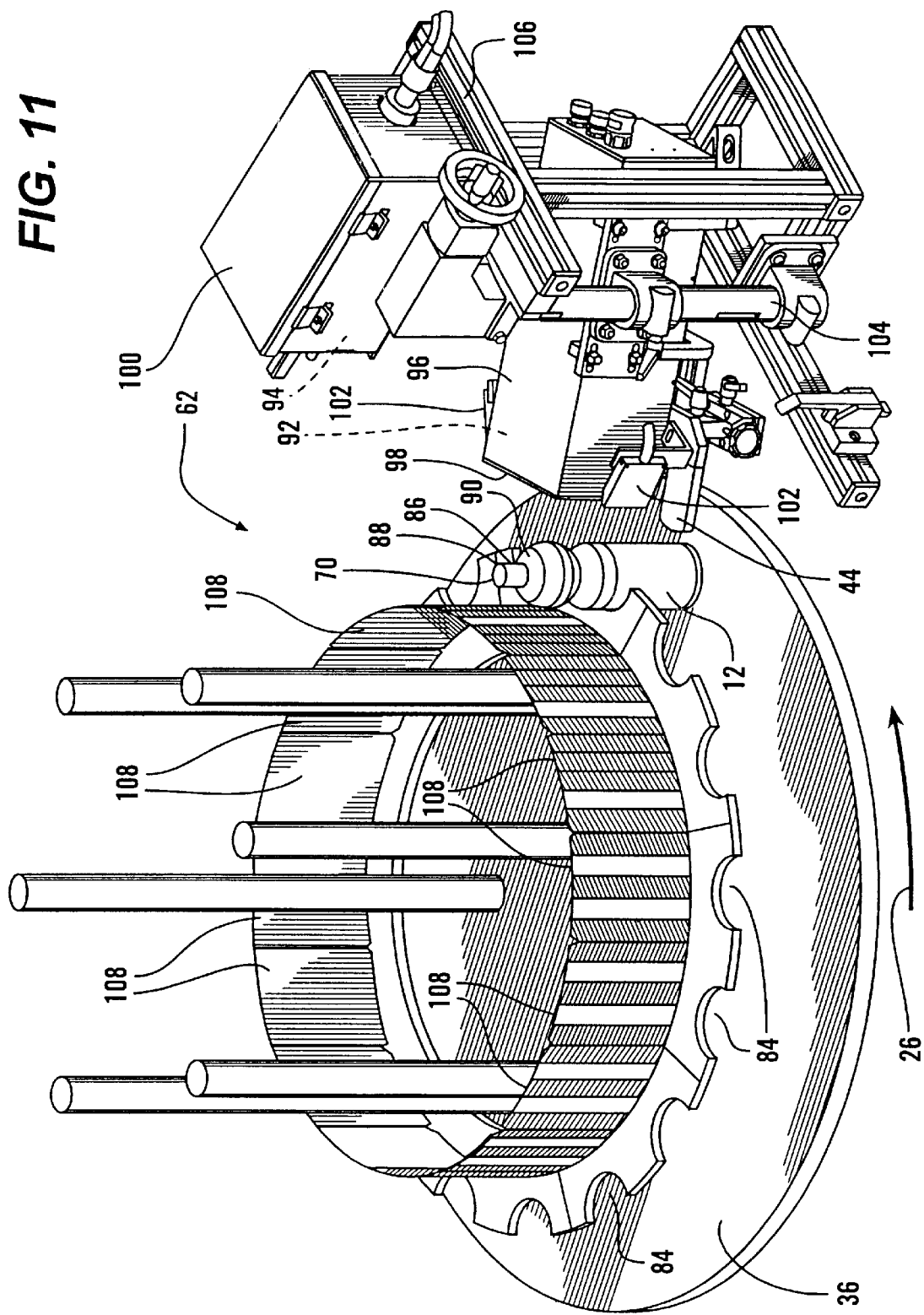
FIG. 11 is a perspective view of the neck finish vision inspection assembly of the system shown in FIG. 1.
Figure 12:
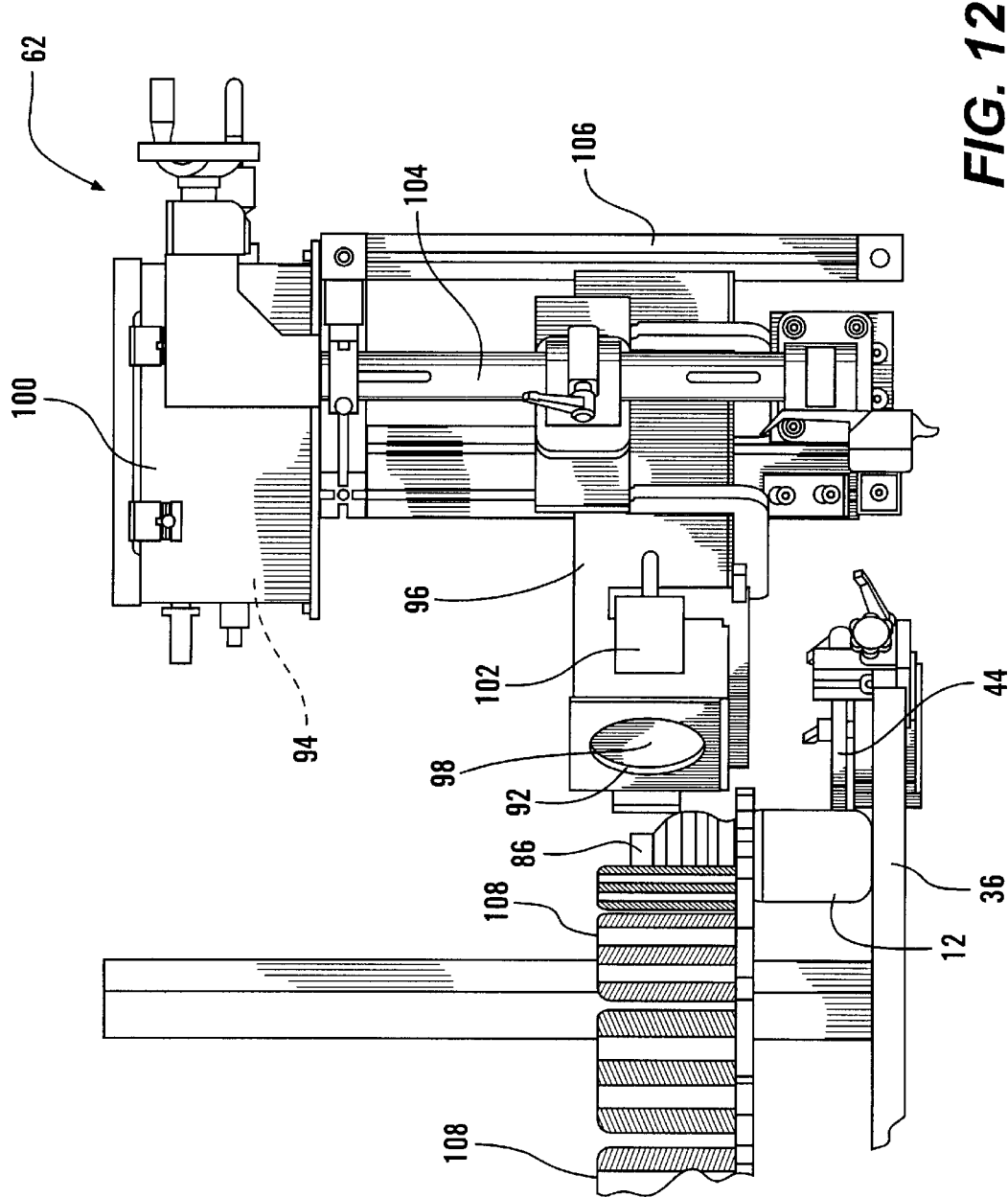
FIG. 12 is a side elevational view of the assembly shown in FIG. 11.

As depicted in FIG. 7, a box 78 containing the camera 72 and a high frequency florescent light source or strobe light 74 is mounted on a frame 80 to provide co-axial illumination (FIG. 8). A preferred camera 72 is a CCD matrix system with at least 250,000 pixels and capable of providing 256 gray levels for each pixel. The assembly 60 includes a vertical position adjuster 82 to slide the box 78 upward and downward and adjust the location of the camera 72 in relation to the container 12. In a preferred embodiment, the camera/lighting enclosure 78 is about 14"(h)×18"(w)×4"(l), and the frame or stand 80 is about 72"(h)×24"(w)×24"(l). The assembly also includes a trigger photoeye unit 44a positioned immediately preceding the infeed starwheel deadplate 40. The photoeye unit 44a is mounted on the frame 80, and can be vertically adjusted according to the height of the container being tested.

As a container 12 moves from the line conveyor 14 and into the infeed starwheel 34, it passes onto the deadplate 40, simultaneously triggering the photoeye unit 44a, which signals the light 74 and the camera 72, to illuminate and image the top seal surface 70 of the container 12. The image is converted to numeric digital images, which are transmitted by a data signaling device to the microprocessor 50. The microprocessor is programmed with TSS inspection algorithms that allow separate specification of rejection limits for size of mechanical defects, such as nicks or scratches, on inner and outer edges of the TSS, maximum allowable TSS width variation and maximum ovality.

From the TSS inspection station 60, the container 12 is transferred from the pocket 76 in the infeed starwheel 34 to a test position 84 in the main turntable 36, and is moved on to the next inspection station.

Neck Finish Vision Inspection/Leak Test

The system 10 advantageously incorporates a neck finish or thread dimension vision inspection assembly 62, as depicted in FIGS. 11–14.

The inspection can be located on the main turntable 36 (as shown), at either of the two rear corners. The neck 86 of the container, viewed horizontally, is inspected to check for dimensional conformance from the top 88 of the neck 86 to the shoulders 90 of the container 12. The inspection involves the measurement of container thread diameters and dimensions of other nearby features, and requires a diffuse light field on the opposite side of the container from the camera. The neck finish inspection assembly 62 can visually inspect neck diameter, thread 1 diameter, thread 2 diameter, support ring diameter, height from the top of container to the support ring, safety band diameter, thread top, thread bottom, and vertical position of the safety band.

As shown, the neck finish inspection assembly 62 includes an enclosure (box) 96 containing a camera 92, similar to that used for TSS 72, with a telecentric lens 98, and an enclosure (box) 100 containing the light source 92, which is preferably a strobe light. The use of a telecentric lens 98 allows for a variance in the position of the container 12 on the turntable 36 in relation to the camera 92 (forward, backward) within a set area or zone in front of the camera 92, and provides an image that is a constant size regardless of where the container is positioned within the set zone.

The camera 92 and light source 94 are mounted outside the rotary platform 36 that carries the container 12. A photoeye unit 44 is positioned immediately in front of the camera enclosure 96. The enclosures 96, 100 containing the camera 92 and lighting, are mounted on a vertical positioning adjuster 104 on frame 106, and can be vertically repositioned according to the height and dimensions of the container 12 on the main turntable 36. The photoeye unit 44 is mounted on a separately adjustable frame.

The required backlighting of the container 12 is provided by placing a diffuse reflecting surface 108 at each leak inspection position, perpendicular to a radius of the turntable 36 and an appropriate distance toward the center of the turntable from each leak inspection position. The reflecting surface 108, as shown, is composed of alternating black and white (dark and light) vertical stripping pattern, which provides better definition of the container contour than would be seen with a completely reflective surface. In system 10, illumination of the neck finish is provided by a single light source 94 housed in the enclosure 100 which is connected to and split by fiber optic light guides 102 located on either side of the camera 92. The illumination can also be provided by two light sources positioned in relation to the camera similar to the fiber-optic guides 102. The light guides 102 (or two light sources) are positioned and controlled to illuminate only the reflecting surface 108, not the container directly.

Figure 14:
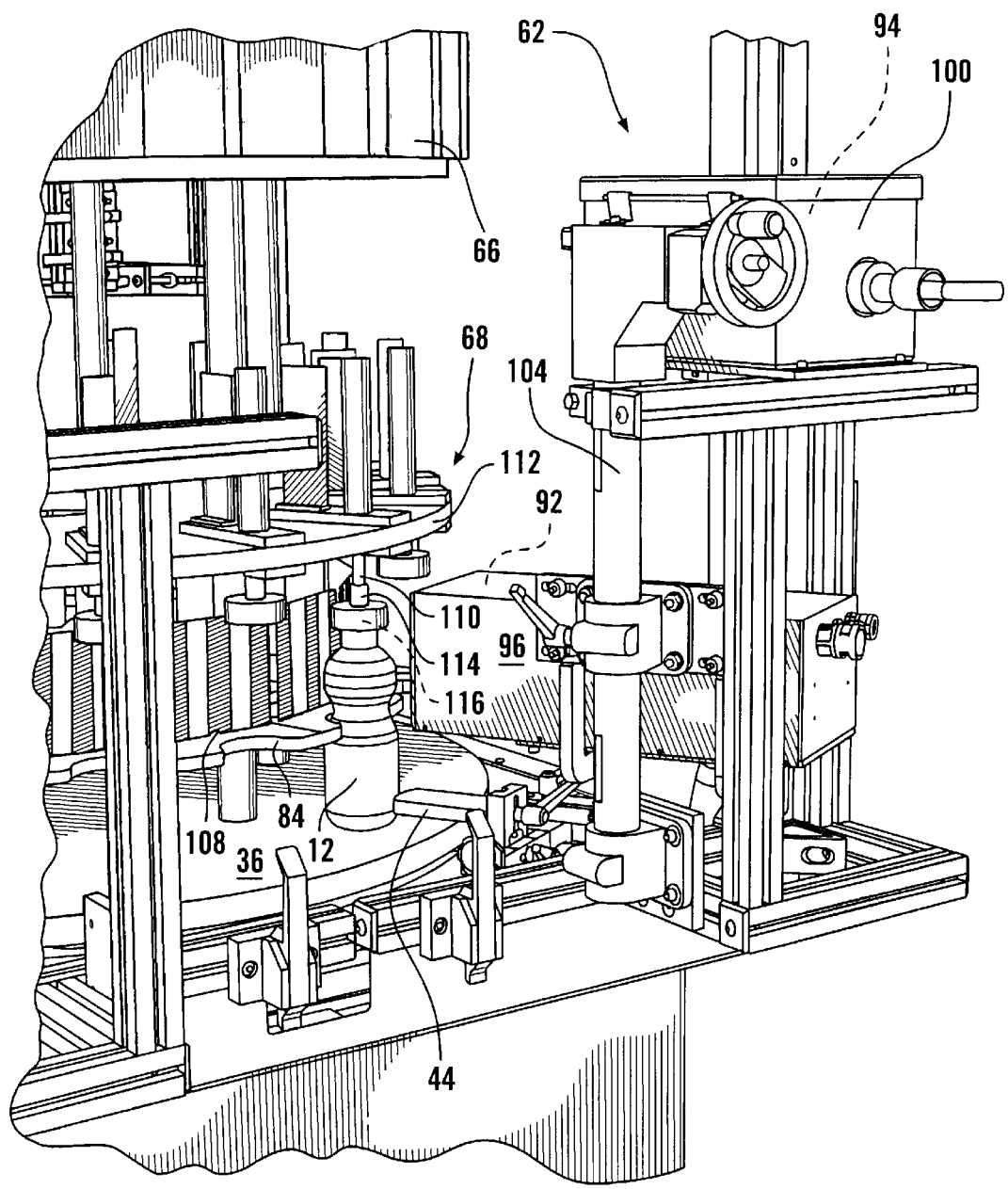
FIG. 14 is a perspective side view of the assembly shown in FIG. 9, showing the integration of the leak inspection assembly into the system.

In the preferred embodiment, the system integrates the neck finish (thread dimension) inspection with a leak test assembly to test the integrity of the entire container, as depicted in FIG. 14. The leak detection assembly 68 is composed of a downwardly extending plunger 110 (test probe piston) that is mounted on a carriage 112 for vertical movement. The plunger 110 includes a sealing means 116, such as a disc, and a vent or port 114 for passing air into the container 12.

It was found that by locating the neck finish inspection assembly 62 on the main turntable 36 in conjunction with the leak test assembly 68, the contact of the plunger 110 holds the container 12 in a highly consistent position for imaging the thread dimensions and other related features, and eliminates position variation due to the container bouncing or rocking. This results in improved accuracy and reproducibility of dimensional measurements.

However, the disc 116 providing the leak testing seal can partially obscure the view of the very top of the neck, i.e., the top seal surface (TSS) 70 in side view, which can interfere with the accurate measurement of the vertical distance from the TSS 70 to some lower feature, such as the vertical distance from the TSS to the support (neck) ring. If this measurement is desired, that particular finish inspection measurement can be performed at the exit starwheel 38 where the finish dimension and base inspection camera/lighting positions do not interfere with one another (not shown). In this position, an emitting backlight field can be located above the centerguide 32 with the camera "looking" horizontally across the starwheel 38. The camera detects the height of the sealing surface at a plurality of points by detecting a minimum in the light beam. Variations in the height indicate sealing surface defects such as a narrow depression or "dip" in the bottle mouth, or a wide depression or "saddle."

If such dimensions relative to the TSS are not required, it is preferred to perform the neck finish inspection on the main turntable in conjunction with the leak test. At the completion of the TSS inspection and as the container moves along the main turntable 36, a stationary metal target triggers a proximity switch (not shown) that is positioned on a control disc above the leak testing assembly 68, causing the plunger 110 of the leak detection assembly 68 to move downwardly onto the seal surface 70 of the container 12, and the disc 114 to contact the top seal surface 70 of the container. The container is then filled with air, and the air pressure within the container is monitored over a set time period. If a minimum pressure in the container 12 is not reached at the end of that period, the data is communicated through a data signaling device to the leak testing control unit 66 resulting in the container being rejected as leaky. The air pressure in the container is then monitored over a set time period and, if the pressure decreases over that period to a predetermined value, the container is classified as leaky, resulting in the container being rejected. Leak test sensitivity depends on the shape, volume and material of the container, and the dwell time period available at the required testing speed. Sensitivity generally ranges from 0.002" diameter holes for small rigid containers, to 0.02" diameter holes for large, flexible, flat sided containers.

In conjunction with the leak test, the container can also be tested for topload deflection. When the plunger 110 is moved downward and the disc 116 is pushed onto the top seal surface 70, a topload (vertical) force is applied to the container 12. The container is tested to check if it can withstand and not crush under a predefined vertical force. Sensors (not shown) mounted to the plunger 110 are adjusted to provide a signal when the plunger 110 is at the correct height for a good container. If the container crushes or deflects under the vertical force, the sensor turns off and the data is communicated to the leak test controller 66 resulting in the container being rejected.

In the present system 10, the neck finish vision inspection is conducted during the monitoring period of the leak test (FIG. 14). As the container and probe are moved along the main turntable 36, the container triggers the photoeye 44b connected to the neck finish assembly 62, which activates the vision inspection operation.

Figure 13:
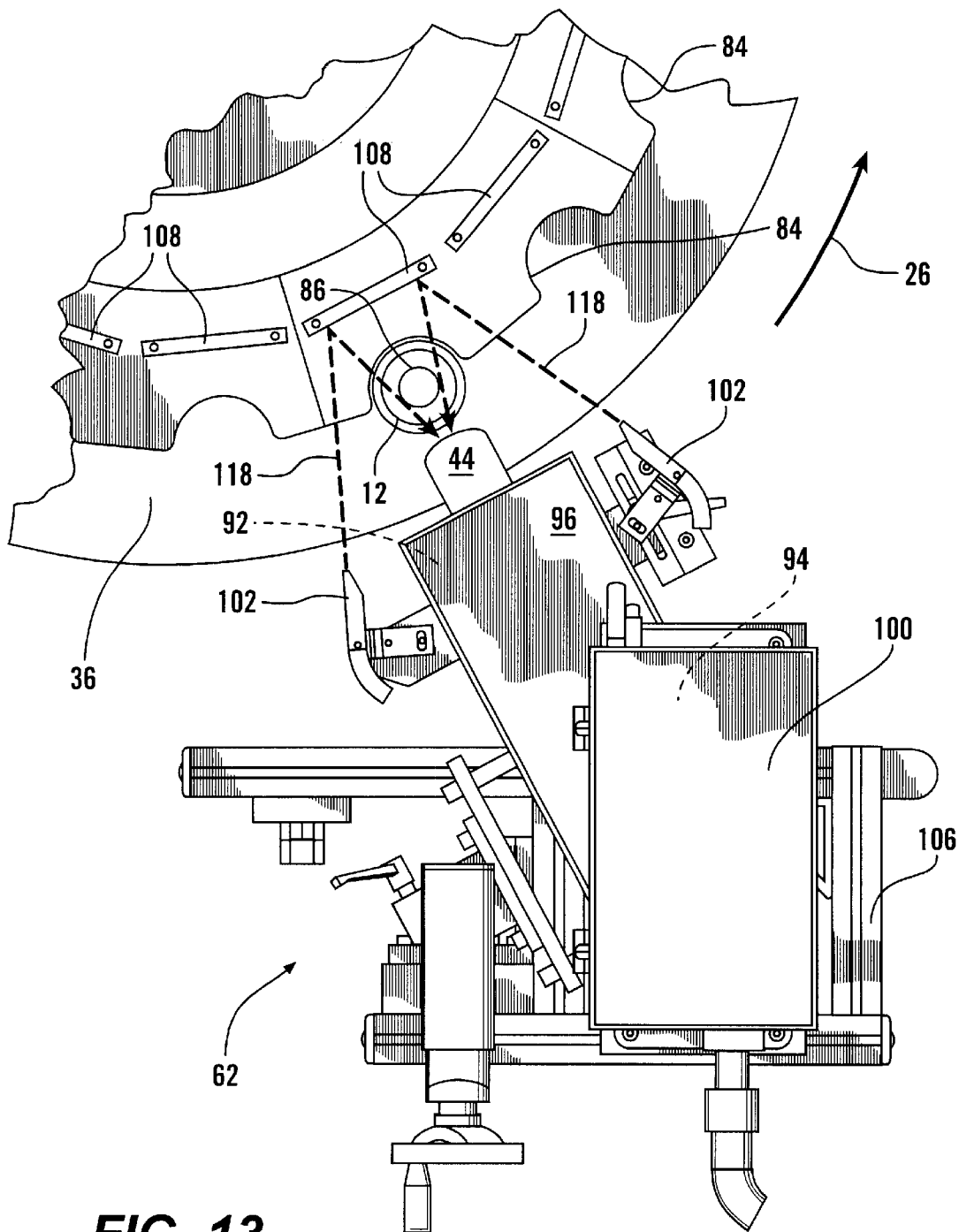
FIG. 13 is a top plan view of the assembly shown in FIG. 11.

The light source 94, preferably a strobe light, is triggered and light is directed from the fiber-optic light guides 102 toward the reflective surface 108, and the backlighting is projected horizontally above and through the neck finish portion of the container 12, as depicted by pathway 118 (FIG. 13). The camera images the neck area 86 of the container, and the data is extracted from the camera image. Software converts the data to values that directly indicate measurements of various neck dimensions. If any measurements exceed the predetermined limits, the container is rejected.

After completion of the neck finish vision inspection and the leak test monitoring period, the plunger 110 retracts and the container 12 is moved along the main turntable 36 to the next station.

Neck Fold Inspection

Neck fold defects occur in the shoulder 90 of the container 12 below the finish. These defects are composed of horizontal regions of thicker plastic. A neck fold inspection system inspects the top region of clear containers, viewing horizontally, to check for partial neck folds where there is thickening of the container wall in the neck region.

Neck folds can be detected in the same camera image that is analyzed for neck finish dimensions (FIGS. 11–14) if the field of view is enlarged to include this area of the container. This is accomplished by using a different camera lens. However, the enlarged field of view can cause a reduction in the dimensional accuracy (resolution) of the finish dimension inspection. To avoid degrading performance of neck finish dimension inspections, the neck fold inspection can be done at a separate location on the turntable 36, with a separate camera and similar light source. Presence of the leak testing seal does not affect the neck fold inspection.

A neck fold inspection assembly (not shown) can be integrated into the present system 10 along the main turntable at the rear corner of the upper frame 18 where the neck finish station is not located.

Base Inspection

As the container 12 is moved along in the direction of arrow 119, it is eventually transferred from the position 84 on the main turntable 36 to a pocket 120 in the exit starwheel 38 where the base vision inspection assembly 64 is installed, as depicted in FIGS. 15–18. The base vision inspection system 64 visually images the base 122 of a clear container, viewing vertically through the opening 124 of the neck 86, to detect concentricity of the gate, presence of "poly-rings," and, where evident from the image, cracks in the gate area.

During the base inspection, the position of the "gate," a feature created when the preform is injection molded, is located relative to one or more features created by the blow molding process. The deviation of the gate from the center of the blow molded features is measured. Rejection of the container occurs if the deviation exceeds predetermined limits set by the operator. Statistically monitoring the gate deviations over a series of containers allows correcting the process problem before it exacerbates into numerous container rejections.

Other base defects that are detected as part of this inspection can include base cracks, and excessive "crystallinity," a defect that is introduced in the preform molding process. Small holes in the gate are not typically detectable by vision inspection.

Base inspection optimally requires positioning the light source 126 to provide backlighting from below the container 12, with a camera 128 located above the container 12. It was determined that, because of the lighting requirement, the preferred site for the base inspection is where the bottle passes over one of the two deadplates 40, 42 between the main turntable 36 and the line conveyor 14. In the present system 10, with the infeed starwheel deadplate 40 being occupied by the top seal surface inspection assembly 60, the base inspection assembly 64 is shown installed at the exit starwheel 38. As with the infeed starwheel 34, the shape and size of the pockets 120 of the exit starwheel 38 are adapted to optimize container position for the base vision inspection.

Figure 15:
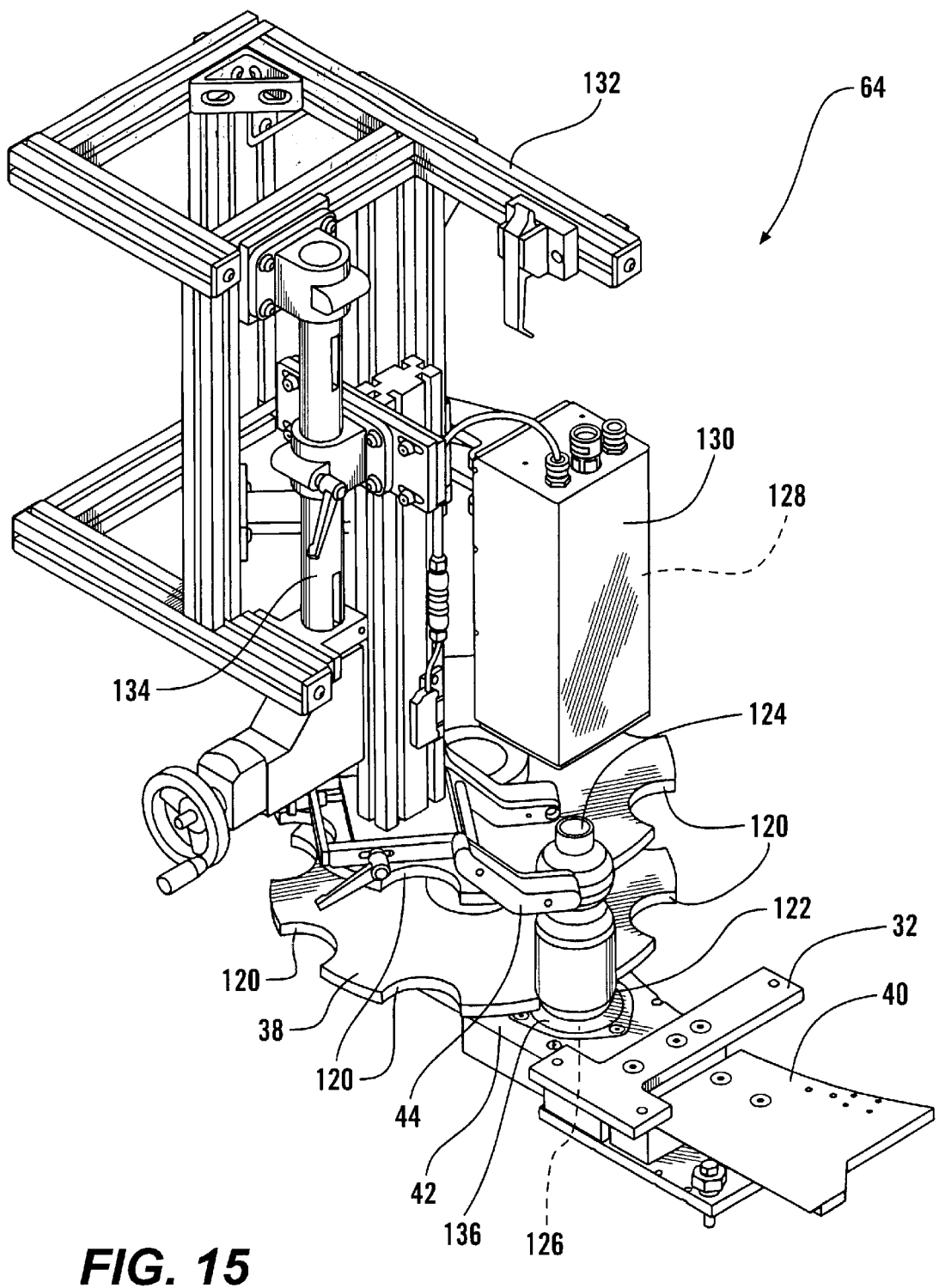
FIG. 15 is a perspective view of the base vision inspection assembly of the system shown in FIG. 1.
Figure 16:
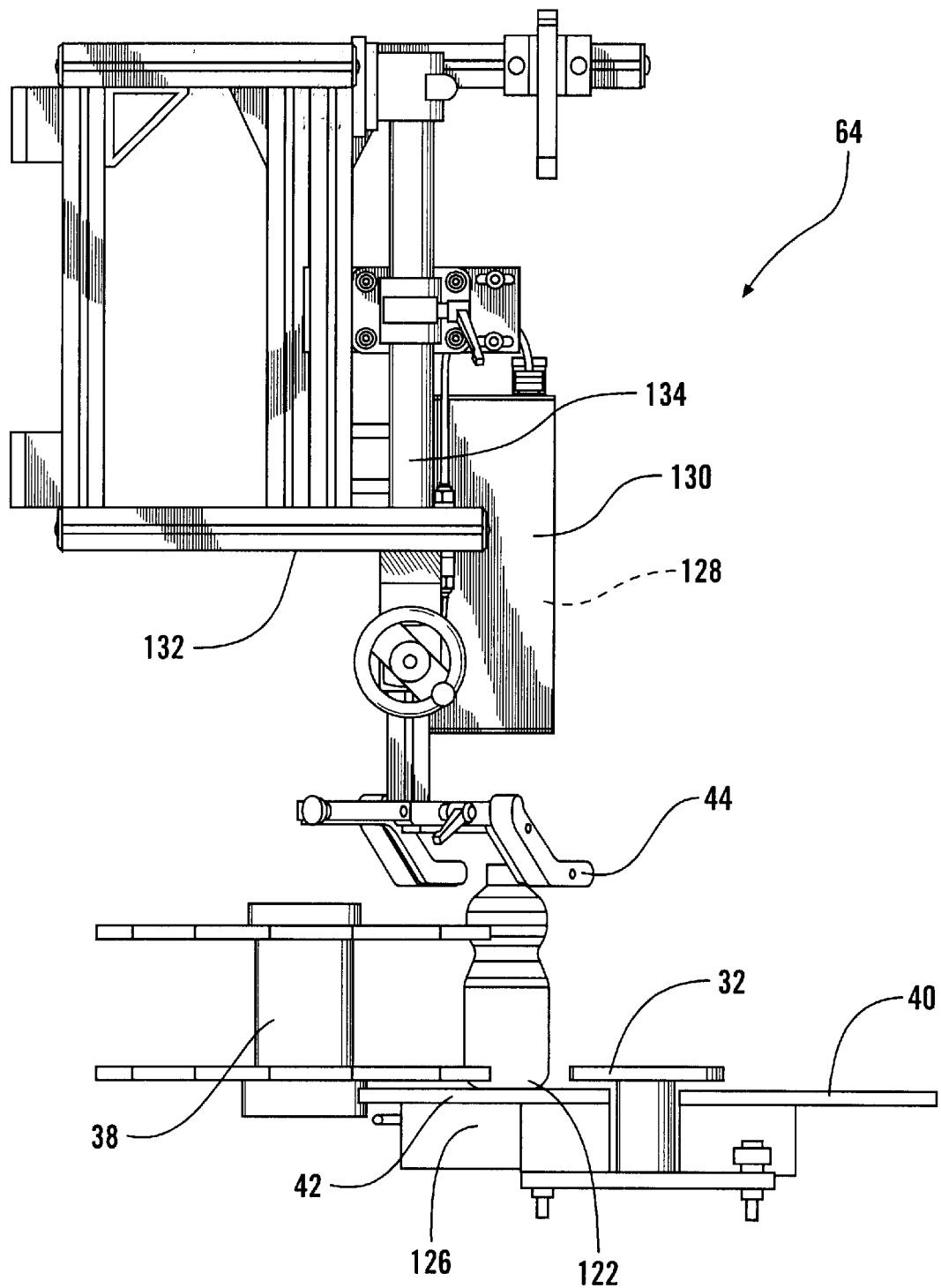
FIG. 16 is a side elevational view of the assembly shown in FIG. 15.
Figure 17:
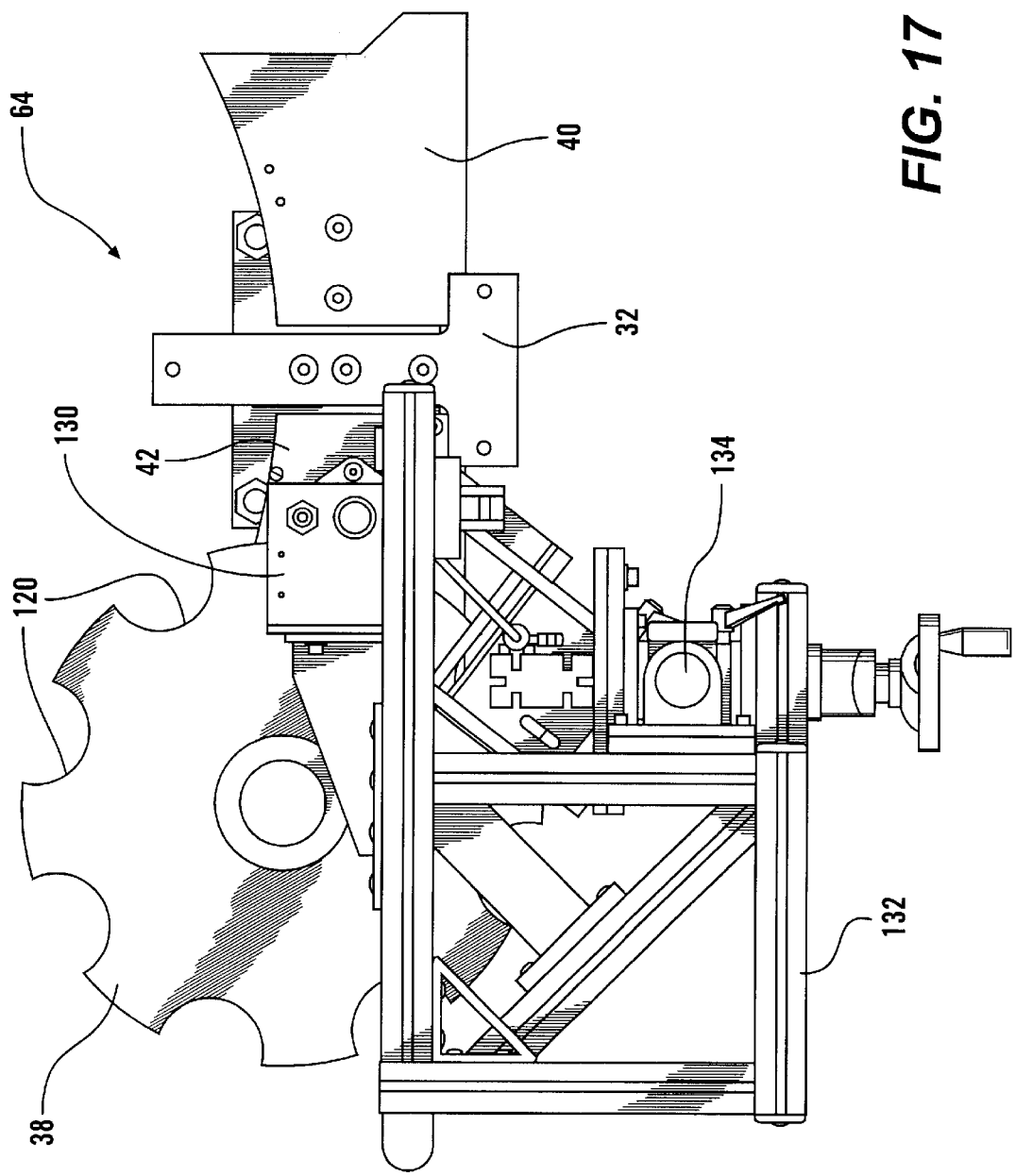
FIG. 17 is a top plan view of the assembly shown in FIG. 15.
Figure 18:
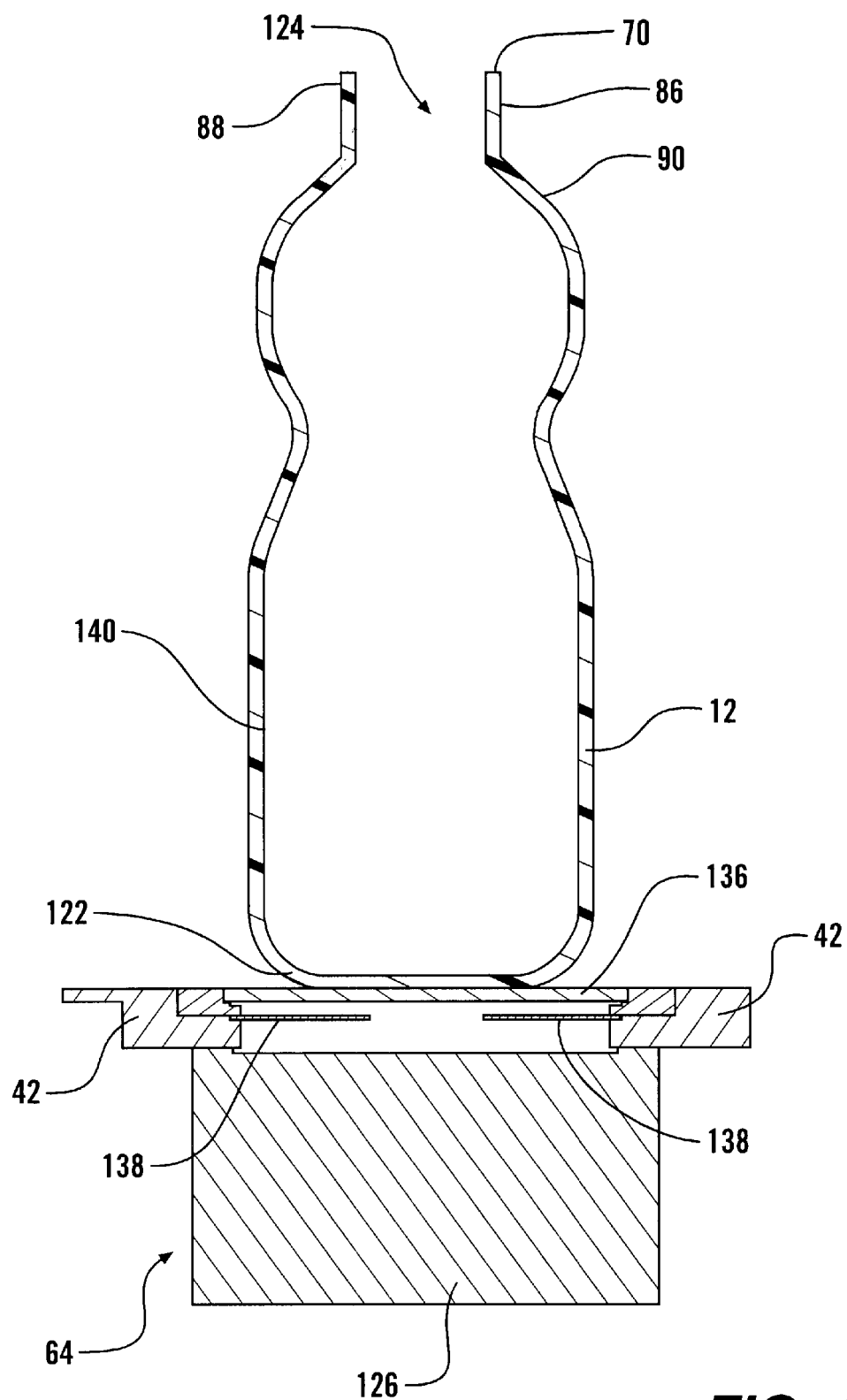
FIG. 18 is a side elevational and cross-sectional view of a container positioned on the deadplate of the base vision inspection assembly shown in FIG. 15.

As depicted in FIG. 15, an enclosure (box) 130 containing a camera 128 similar to 72 is mounted on a frame assembly 132 that includes a vertical position adjuster 134 for sliding the box 130 upward and downward to adjust the location of the camera 128 in relation to the container 12 on the deadplate 42. The assembly 64 also includes a trigger photoeye 44c mounted on the frame 132, which can be vertically adjusted according to the height of the container. The photoeye 44c is positioned immediately preceding the deadplate 42 at the exit starwheel 38 so that movement of the container 12 onto the deadplate 42 will trigger the photoeye 44c which, in turn, triggers the camera 128. Typically, this inspection does not require a strobe light as some degree of image blurring (due to container speed) is acceptable.

Illumination of the base 122 of the container 12 is provided by a high frequency lighting source 126 mounted beneath the deadplate 42 of the exit starwheel 38, which projects light through a "window" 136 in the deadplate 42. The window 136 is composed of a diffuse or semi-transparent glass or plastic material, and can include a mounting for a focusing lens, light diffuser, an iris, and/or interchangeable aperture plates or disks 138 to control the size of the opening 140 through the window 136 for the light source 126. Using an aperture disk 138 that is matched to the geometry, i.e., size and shape, of a particular bottle base 122 to control the amount of the light enhances and provides a sharper camera image and greater contrast of the features surrounding the gate area of the container 12.

Data is again extracted from the camera image and converted by the microprocessor 50 to values that directly indicate the gate position relative to molded container features as well as size and location of other defects. If any dimensions exceed predetermined limits set by the operator, the container is rejected.

Sidewall Inspection

A sidewall inspection system checks the body 140 of the container for inclusions, bubbles, black spots, major pinholes, and deformation. All sides of the container are viewed, which can be accomplished by a) two or more cameras mounted about 85–90° apart, preferably about 90° apart, and directed horizontally across the support surface (not shown), or b) rotation of the container as it moves past a single camera mounted to project horizontally across the support surface (not shown but similar to the camera arrangement in FIGS. 11–13). A diffuse light source is positioned behind the container (opposite the camera) to illuminate the body 140 of the bottle by backlighting so that opacities show as dark images.

This inspection is preferably performed with multiple cameras mounted in an assembly along the line conveyor 14 downstream of the exit starwheel 38 and preceding the rejection station 142. At this point, the containers are regularly spaced, generally on about minimum 5.5" centers, allowing multiple cameras to view all sides of the container. As an alternative, a sidewall vision inspection assembly can be installed along the main turntable preferably in one of the two rear corners of the upper frame 18.

Rejection Station

From the base vision inspection station 64, the container 12 is moved out of the exit starwheel 38 and back onto the line conveyor 14, and onto the final rejection station 142. The rejection station 142 includes a "reject kicker" or blow-off nozzle 144 that physically removes or diverts defective containers from the line conveyor 14, for example, into a container 146 or a chute. The reject kicker 144 can be, for example, a pneumatically-operated kicker device, an air reject, a reject cylinder, or other similar mechanism. The reject kicker 144 responds to a signal from the PLC 48 that represents an acceptable or unacceptable container, and includes a memory queue to track successive containers. The shift of a particular container 12 through the system 10 and to the rejection point 142 corresponds to the "sync" signal set by the PLC 48 at the start of the operation, so that the appropriate container is ejected from the system. As the container 12 moves past the reject station 142, a signal from the PLC 48 triggers the reject kicker 144 if the container 12 has been rejected at any one of the test stations and fails to meet the set parameters programmed into the microprocessor 50 of the leak test controller 66.

Defective product that is ejected and not shipped to the end customer, provides an "early warning" detection system to alert operators of process drifts that are creating defects. The system can thus be used to monitor production line performance and generate detailed production data.

The invention has been described by reference to detailed examples and methodologies. These examples are not meant to limit the scope of the invention. Variations within the concepts of the invention are apparent to those skilled in the art. The disclosures of the cited references throughout the application are incorporated by reference herein.

What is claimed is:

1. An integrated inspection system for visually inspecting a container for defects, the container having a mouth with a top seal surface, neck, shoulder, side surface, and base; the system comprising:

a series of visual inspection stations, each comprising a surface to support the container thereon, and an assembly to inspect a select portion of the container;

an infeed mechanism to move the container into the system;

an exit mechanism to move the container out of the system;

a conveyor to move the container through the system; and a microprocessor to receive and analyze data signals received from the visual inspection stations and generate data relating to the container;

wherein the series of visual inspection stations, includes:

a) a first visual inspection station to inspect the top seal surface of the container, the top seal surface inspection assembly including:

a light source mounted in a vertical orientation to illuminate the top seal surface of the container when positioned on the support surface;

a camera mounted in a vertical orientation to image the top seal surface of the container when positioned on the support surface; and a data signaling device connected to the camera and the microprocessor, to receive a data signal from the camera representative of the camera image of the top seal surface of the container and transmit the data signal to the microprocessor;

b) a second visual inspection station to inspect the neck finish of the container, the neck finish inspection assembly including:
  a light source mounted horizontally to direct illumination over the support surface;
  a reflective surface positioned to receive and reflect the illumination toward the neck of the container when positioned on the support surface;
  a camera mounted horizontally to image the neck of the container when positioned on the support surface;
  a data signaling device connected to the camera and the microprocessor, to receive a data signal from the camera representative of the camera image of the neck of the container and transmit the data signal to the microprocessor; and c) a third vial inspection station to inspect the base of the container, the support surface structured to allow light to pass therethrough, and the base inspection assembly including:
  a light source mounted beneath the support surface to illuminate the base of the container when positioned on the support surface;
  a camera mounted in a vertical orientation to image the base of the container through the neck when the container is positioned on the support surface; and
  a data signaling device connected to the camera and the microprocessor, to receive a data signal from the camera representative of the camera image of the base of the container and transmit the data signal to the microprocessor; and wherein the conveyor comprises the infeed mechanism to convey the container into the first visual inspection station and the exit mechanism to convey the container out of the third visual inspection station.

2. The inspection system according to claim 1, further comprising:
  a photosensitive detector (photoeye) positioned at a location in advance of each visual inspection station, to sense the presence of the container and send a signal to the microprocessor to initiate an inspection operation sequence.

3. The inspection system according to claim 1, further comprising a video screen, a printer, or a combination thereof, connected to the microprocessor to display the generated data.

4. The inspection system according to claim 1, further comprising a mechanism to eject a defective container from the system, positioned along a line conveyor situated downstream from the exit mechanism, and connected to the microprocessor;
  wherein the microprocessor is programmed to analyze the data signals received from the data signaling devices of the inspection stations and send a signal to the container eject mechanism to move the container off of the line conveyor based upon a predetermined criteria.

5. The inspection system according to claim 1, wherein the conveyor is a continuously moving conveyor belt, a rotating turntable, or a combination thereof.

6. The inspection system according to claim 1, wherein the infeed and exit mechanisms are starwheels, and the container support surfaces are deadplates.

7. The inspection system according to claim 1, wherein the camera and the light source of the top seal surface inspection assembly are co-axially mounted on a frame and vertically adjustable to modify the position of the light source and the camera in relation to the mouth of the container when positioned on the support surface.

8. The inspection system according to claim 1, wherein the light source of the neck finish inspection assembly is connected to fiber-optic light guides mounted on the camera, and the camera is mounted on a frame and vertically adjustable to modify the position of the light guides and the camera in relation to the neck of the container when on the support surface.

9. The inspection system according to claim 1, wherein the camera of the base inspection assembly is mounted on a frame and vertically adjustable to modify the position of the camera in relation to the height of the container on the support surface.

10. The inspection system according to claim 1, wherein the camera of the neck finish inspection assembly has a telecentric lens and is mounted horizontally to image the neck of the container when the container is positioned on the support surface within a set zone within the station.

11. An integrated inspection system for visually inspecting a container for defects, the container having a mouth with a top seal surface, neck, shoulder, side surface, and base; the system comprising:
  a series of visual inspection stations, each comprising a surface to support the container thereon, and an assembly to inspect a select portion of the container;
  an infeed mechanism to move the container into the system;
  an exit mechanism to move the container out of the system;
  a conveyor to move the container through the system; and
  a microprocessor to receive and analyze data signals received from the visual inspection stations and generate data relating to the container;
  wherein the series of visual inspection stations, includes:
    a) a visual inspection station to inspect the top seal surface of the container, the top seal surface inspection assembly including:
      a light source mounted in a vertical orientation to illuminate the top seal sure of the container when positioned on the support surface;
      a camera mounted in a vertical orientation to image the top seal surface of the container when positioned on the support surface; and
      a data signaling device connected to the camera and the microprocessor, to receive a data signal from the camera representative of the camera image of the top seal surface of the container and transmit the data signal to the microprocessor;
    b) a visual inspection station to inspect the neck finish of the container, the neck finish inspection assembly including:
      a light source mounted horizontally to direct illumination over the support surface;
      a reflective surface positioned to receive and reflect the illumination toward the neck of the container when positioned on the support surface;
      a camera mounted horizontally to image the neck of the container when positioned on the support surface;
      a data signaling device connected to the camera and the microprocessor, to receive a data signal from the camera representative of the camera image of the neck of the container and transmit the data signal to the microprocessor; and c) a visual inspection station to inspect the base of the container, the support surface structured to allow light to pass therethrough, and the base inspection assembly including:
a light source mounted beneath the support surface to illuminate the base of the container when positioned on the support surface;
a camera mounted in a vertical orientation to image the base of the container through the neck when the container is positioned on the support surface; and
a data signaling device connected to the camera and the microprocessor, to receive a data signal from the camera representative of the camera image of the base of the container and transmit the data signal to the microprocessor; and wherein the reflecting surface is composed of alternating black and white stripes.

12. The inspection system according to claim 1, wherein the top seal surface inspection assembly is positioned within the infeed mechanism, and the infeed mechanism is structured to convey the container onto the container support surface for the inspection operation, and off the support surface and onto the conveyor to move the container to a subsequent inspection station.

13. The inspection system according to claim 1, wherein the base inspection assembly is positioned within the exit mechanism, and the exit mechanism is structured to convey the container onto the container support surface for the inspection operation, and off the support surface and onto a line conveyor to move the container out of the inspection system.

14. The inspection system according to claim 1, wherein the support surface of the base inspection assembly comprises a semi-transparent material.

15. The inspection system according to claim 1, wherein the support surface of the base inspection assembly comprises a focusing lens, a light diffuser, an iris, an interchangeable lighting aperture plate, or a combination thereof, to control the size of the opening for the light through the support surface.

16. The inspection system according to claim 1, further comprising a leak testing assembly to test integrity of the container, the leak testing assembly comprising:
a downwardly extending plunger mounted on a carriage for vertical movement, a disc affixed to one end of the plunger to contact and seal the mouth of the container, and a port/opening to inject air into the container; and
a data signaling device connected to the microprocessor, to receive a data signal from a first position sensor to commence movement of the plunger onto the mouth of the container, receive a data signal from the plunger representative of air pressure within the container over a set time period, transmit said air pressure data signal to the microprocessor, and receive a signal from a second position sensor to commence movement of the plunger off of the mouth of the container.

17. The inspection system according to claim 16, wherein the plunger is structured to apply a predefined vertical force to the container to test topload deflection, and the plunger includes a sensor to transmit a signal when the disc of the plunger is at a predetermined height for the container, and the data signaling device receives a data signal from the plunger representative of the location of the location of the disc in relation to the predetermined height of the container, and transmits said data signal to the microprocessor.

18. The inspection system according to claim 16, wherein the leak testing assembly is mounted to test the container as it is conveyed through a visual inspection station.

19. The inspection system according to claim 1, further comprising an assembly to inspect the sidewall of the container, the sidewall inspection assembly comprising
a support surface for the container;
two or more cameras mounted horizontally and about 90° apart, to image the sidewall of the container when on the support surface; and
a diffuse light source mounted to backlight the container when positioned on the support surface.

20. The inspection system according to claim 1, further comprising an assembly to inspect the sidewall of the container, the sidewall inspection assembly comprising
a surface to support and rotate the container;
a camera mounted horizontally to image the sidewall of the container when positioned on the support surface; and
a diffuse light source mounted to backlight the container when positioned on the support surface.

21. The inspection system according to claim 1, wherein the sidewall inspection assembly is mounted along a line conveyor downstream from the exit mechanism.

22. An integrated inspection system for visually inspecting a container for defects, the container having a mouth with a top seal surface, neck, shoulder, side surface, and base; the system comprising:
an infeed starwheel to move the container from a line conveyor and into the system;
an exit wheel to move the container out of the system and onto a line conveyor;
a main conveyor to continuously move a series of containers along a pathway through a series of visual inspection stations;
a microprocessor to receive and analyze data signals received from the visual inspection stations and generate data relating to the container based upon predetermined criteria;
wherein the series of visual inspection stations, includes:
a) a first visual inspection station positioned within the infeed starwheel, and comprising an assembly to inspect the top seal surface of the container, the top seal surface inspection assembly including:
a deadplate to support the container thereon,
a light source mounted to illuminate the top seal surface of the container;
a camera mounted in a vertical orientation to image the top seal surface of the container; and
a data signaling device connected to the camera and the microprocessor, to receive a data signal from the camera representative of the camera image of the top seal surface of the container and transmit the data signal to the microprocessor;
b) a second visual inspection station positioned along the main conveyor downstream from the first inspection station, and comprising an assembly to inspect the neck finish of the container, the neck finish inspection assembly including:
a surface to support the container thereon;
a light source mounted to provide a horizontally directed light beam;
a reflective surface positioned to receive and reflect the light beam to illuminate the neck of the container when positioned on the support surface;
a camera directed horizontally to image the neck area of the container when positioned on the support surface; and a data signaling device connected to the camera and the microprocessor, to receive a data signal from the camera representative of the camera image of the neck of the container and transmit the data signal to the microprocessor; and c) a third visual inspection station positioned within the exit starwheel, and comprising an assembly to insect the base of the container, the base inspection assembly including:

a deadplate to support the container thereon, and structured to allow passage of light therethrough;

a light source mounted beneath the deadplate to direct light through the deadplate and onto the base of the container;

a camera mounted in a vertical orientation to image the base of the container; and a data signaling device connected to the camera and the microprocessor, to receive a data signal from the camera representative of the camera image of the base of the container and transmit the data signal to the microprocessor; and wherein the main conveyor comprises the infeed starwheel to convey the container into the first visual inspection station and the exit starwheel to convey the container out of the third visual inspection station and onto the line conveyor.

23. An integrated inspection system for visually inspecting a container for defects, the container having a mouth with a top seal surface, neck, shoulder, side surface, and base; the system comprising:

a) a conveyor to move the container through the system;
b) a series of visual inspection stations, each including:
   i) a surface to support the container thereon, and
   ii) an assembly to inspect a select portion of the container, including:
      a light source mounted to illuminate the select portion of the container,
      a camera mounted to image the select portion of the container, and
      a data signaling device connected to the camera to receive a data signal from the camera representative of the camera image;
c) a microprocessor connected to the data signaling device of each of the inspection stations to receive and analyze data signals from the data signaling device, and generate data relating to the container based upon predetermined criteria;

the series of visual inspection stations including:

a first station comprising a top seal surface inspection assembly including a light source mounted in a vertical orientation to illuminate the top seal of the container, and a camera mounted in a vertical orientation to image the top seal of the container;

a second station comprising a neck finish inspection assembly including a light source mounted to provide a horizontally-oriented light beam, a reflective surface positioned to receive and reflect the fight in a horizontal orientation to illuminate the neck of the container when positioned on the support surface of said assembly, and a camera mounted in a horizontal orientation to image the neck of said container; and a third station comprising a base inspection assembly including a light source mounted beneath the support surface of said assembly to direct light through the support surface to imitate the base of the container, and a camera mounted in a vertical orientation to image the base through an opening in the neck of the container; and wherein the conveyor comprises an infeed mechanism to convey the container into the first station, an exit mechanism to convey the container out of the third station, and a rotatable turntable to convey the container from the infeed mechanism to the exit mechanism.

24. A method of visually inspecting for defects in a container having a mouth with a top seal surface, neck, shoulder, side surface, and base comprising:

conveying the container into an infeed starwheel and onto a support surface of a first visual inspection station comprising an assembly to visually inspect the top seal surface of the container;

visually inspecting the top seal surface of the container by activating a light source and camera mounted in the assembly to illuminate and image the top seal surface of the container while the container is positioned on the support surface of said assembly, wherein a data signal is generated by the camera representative of the image and transmitted to a microprocessor;

conveying the container onto a support surface of a second visual inspection station comprising an assembly to visually inspect the neck of the container;

visually inspecting the neck of the container by activating a light source and a camera mounted in the assembly to direct a light beam toward a reflective surface positioned behind the container to indirectly illuminate and image the neck of the container while the container is positioned on the support surface, wherein a data signal is generated by the camera representative of the image and transmitted to the microprocessor;

conveying the container into an exit starwheel and onto a support surface of a third visual inspection station comprising an assembly to visually inspect the base of the container;

visually inspecting the base of the container by activating a light source and camera mounted in the assembly to illuminate and image the base of the container while the container is positioned on the support surface, wherein a data signal is generated by the camera representative of the image and transmitted to the microprocessor;

conveying the container from the support surface and out of the exit starwheel of the base inspection assembly to a ejection station comprising a device to receive a data signal from the microprocessor relating to the container based upon predetermined criteria, and an assembly to divert the container upon receipt of such data signal indicating a defect in the container; and activating the container diverting assembly to eject a defective container from the system.

25. The method according to claim 24, further comprising:

testing the integrity of the container by activating a plunger having a disc affixed to one end and mounted on a carriage of the system, to move vertically such that the disc seals the mouth of the container, injecting air into the container, testing the air pressure in the container for a set time period, and removing the plunger disc from the mouth of the container at the end of the set time period;

wherein a data signal is generated by a sensor on the plunger representative of the air pressure with the container, and transmitted to the microprocessor.

26. The method according to claim 25, wherein the integrity test is conducted after completion of the visual inspection of the top seal surface of the container, and as the container is conveyed to the second inspection station.

27. The method according to claim 25, further comprising testing the topload deflection of the container by activating the plunger to apply a predefined vertical force to the container, wherein a data signal is transmitted representative of the location of the disc in relation to a predetermined height of the container and transmitted to the microprocessor.

* * * * *